(12) United States Patent
Elroy-Stein et al.

(10) Patent No.: US 9,377,453 B2
(45) Date of Patent: *Jun. 28, 2016

(54) SYSTEMS AND METHODS FOR DETECTION OF CELLULAR STRESS

(71) Applicants: RAMOT AT TEL AVIV UNIVERSITY LTD., Tel Aviv (IL); ANIMA CELL METROLOGY, INC., Bernardsville, NJ (US)

(72) Inventors: Orna Elroy-Stein, Tel-Aviv (IL); Marcelo Ehrlich, Tel-Aviv (IL); Sima Barhoom, Hod Hasharon (IL); Zeev Smilansky, M.P. Emek Soreq (IL)

(73) Assignees: RAMOT at Tel Aviv University Ltd., Tel-Aviv (IL); Anima Cell Metrology, Inc., Bernardsville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,647

(22) Filed: Aug. 19, 2015

(65) Prior Publication Data

US 2016/0033479 A1 Feb. 4, 2016

Related U.S. Application Data

(63) Continuation of application No. 13/811,370, filed as application No. PCT/IL2011/000584 on Jul. 21, 2011, now Pat. No. 9,140,650.

(60) Provisional application No. 61/366,550, filed on Jul. 22, 2010, provisional application No. 61/451,135, filed on Mar. 10, 2011.

(51) Int. Cl.
*C12Q 1/68* (2006.01)
*G01N 33/50* (2006.01)
*G01N 21/64* (2006.01)

(52) U.S. Cl.
CPC .......... *G01N 33/5035* (2013.01); *C12Q 1/6841* (2013.01); *G01N 21/6428* (2013.01); *G01N 21/6486* (2013.01); *G01N 2021/6439* (2013.01)

(58) Field of Classification Search
None
See application file for complete search history.

(56) References Cited

U.S. PATENT DOCUMENTS 7,288,372 B2 10/2007 Olejnik
9,140,650 B2 * 9/2015 Elroy-Stein .......... C12Q 1/6841

2003/0092031 A1 5/2003 Rothschild
2003/0219780 A1 11/2003 Olejnik
2004/0235175 A1 11/2004 Gaudernack

FOREIGN PATENT DOCUMENTS

| WO | 94/02595 | 2/1994 |
| WO | 03/057164 | 7/2003 |
| WO | 2004/050825 | 6/2004 |
| WO | 2009/047760 | 4/2009 |

OTHER PUBLICATIONS

Akhtar and Juliano (1992) Cellular uptake and intracellular fate of antisense oligonucleotides. Trends Cell Biol 2(5): 139-144.
Barhoom et al., (2011) Quantitative single cell monitoring of protein synthesis at subcellular resolution using fluorescently labeled tRNA. Nucleic acids Res 39(19): e129 and supplementary data.
Bolte and Cordelieres (2006) A guided tour into subcellular colocalization analysis in light microscopy. J Microsc 224(pt 3): 213-232.
Castello et al., (2009) Regulation of host translational machinery by African swine fever virus. PLoS Pathog 5(8): e1000562.
De Angelis (1999) Why FRET over genomics? Physiol Genomics 1(2): 93-99.
Feigner et al., (1987) Lipofection: a highly efficient, lipid-mediated DNA-transfection procedure. Proc Natl Acad Sci USA 84(21): 7413-7417.
Glenn et al., (1993) Delivery of liposome-encapsulated RNA to cells expressing influenza virus hemagglutinin. Methods Enzymol 221: 327-339.
Ha (2001) Single-molecule fluorescence resonance energy transfer. Methods 25(1): 78-86.
Hopper et al., (2010) Cellular dynamics of tRNAs and their genes. FEBS Lett 584(2): 310-317.
Jia et al., (1997) Nonexponential kinetics of a single tRNAPhe molecule under physiological conditions. Proc Nati Acad Sci U S A 7932-7936.
Jun et al., (2008) Fluorescent labeling of cell-free synthesized proteins with fluorophore-conjugated methionylated tRNA derived from in vitro transcribed tRNA. J Microbiol Methods 73(3): 247-251.

(Continued)

*Primary Examiner* — James Martinell
(74) *Attorney, Agent, or Firm* — Rodney J. Fuller; Booth Udall Fuller, PLC

(57) ABSTRACT

There are provided methods for detection and measurement of stress in a cell, the method including introducing a labeled tRNA into the cell and detecting a change in subcellular localization of the labeled tRNA in the cell, based on the signal emitted from the labeled tRNA. There are further provided methods and systems for the generation of a stress index of a living cell. There are further provided methods and systems for detection of stress in a living cell, comprising detection of changes in subcellular localization of labeled tRNA in a cell, wherein the detection is performed in real time.

20 Claims, 4 Drawing Sheets

(56) References Cited

OTHER PUBLICATIONS

Katsafanas and Moss (2007) Colocalization of transcription and translation within cytoplasmic poxvirus factories coordinates viral expression and subjugates host functions. Cell Host Microbe 2(4): 221-228.

Kenworthy (2001) Imaging protein-protein interactions using fluorescence resonance energy transfer microscopy. Methods 24(3): 289-296.

Liu et al., (2005) Efficient RNA interference in zebrafish embryos using siRNA synthesized with SP6 RNA polymerase. Dev Growth Differ 47(5): 323-331.

Lu et al., (1994) Optimization of methods to achieve mRNA-mediated transfection of tumor cells in vitro and in vivo employing cationic liposome vectors. Cancer Gene Ther 1(4): 245-252.

Malone et al., (1989) Cationic liposome-mediated RNA transfection. Proc Natl Acad Sci USA 86(16): 6077-6081.

Olejnik et al., (2005) N-terminal labeling of proteins using initiator tRNA. Methods 36(3): 252-260.

Qin et al., (2009) Mammalian orthoreovirus particles induce and are recruited into stress granules at early times postinfection. J Virol 83(21): 11090-11101.

Rae and Levis (2002) Single-cell electroporation. Pflugers Arch 443(4): 664-670.

Sakamoto et al., (2004) Improvement of dermatitis by iontophoretically delivered antisense oligonucleotides for interleukin-10 in NC/Nga mice. Gene Ther 11(3): 317-324.

Sako et al., (2006) A novel therapeutic approach for genetic diseases by introduction of suppressor tRNA. Nucleic Acids Symp Ser (Oxf) 2006(50): 239-240.

Selvin (2000) The renaissance of fluorescence resonance energy transfer. Nat Struct Biol 7(9): 730-734.

Shaheen et al., (2007) Retrograde nuclear accumulation of cytoplasmic tRNA in rat hepatoma cells in response to amino acid deprivation. Proc Natl Acad Sci U S A 104(21): 8845-8850.

Smith et al., (2006) Reovirus induces and benefits from an integrated cellular stress response. J Virol 80(4): 2019-2033.

Watson et al., (1995) Macromolecular arrangement in the aminoacyl-tRNA.elongation factor Tu.GTP ternary complex. A fluorescence energy transfer study. Biochemistry 34 (24): 7904-12.

Zaitvesa et al., (2006) tRNAs promote nuclear import of HIV-1 intracellular reverse transcription complexes. PLos Biol 4(10): e332.

Hurto et al., (2007) Inorganic phosphate deprivation causes tRNA nuclear accumulation via retrograde transport in *Saccharomyces cerevisiae*. Genetics 176(2): 841-52.

Whitney et al., (2007) Rapid and reversible nuclear accumulation of cytoplasmic tRNA in response to nutrient availability. Mol Biol Cell 18(7): 2678-86.

\* cited by examiner

SYSTEMS AND METHODS FOR DETECTION OF CELLULAR STRESS

RELATED APPLICATION DATA

This application is a continuation of U.S. patent application Ser. No. 13/811,370, filed Jan. 21, 2013 (published as US 2013/0122491), which is the U.S. National Stage of International Application No. PCT/IL2011/000584, filed Jul. 21, 2011, which claims the benefit of U.S. Provisional Application Nos. 61/366,550, filed Jul. 22, 2010, and 61/451,135, filed Mar. 10, 2011, the contents of each of which are herein expressly incorporated by reference in their entireties for all purposes.

FIELD OF THE INVENTION

The present invention relates to systems and methods for detection of cellular stress by detecting changes in tRNA subcellular localization.

BACKGROUND OF THE INVENTION

Transfer RNA (tRNA) is a small ribonucleic acid (RNA) molecule, generally about 74-95 nucleotides that has a key role in protein synthesis in the cytoplasm. The main function of tRNA is to bind to and transfer a specific activated amino acid to a growing peptide (protein) chain at the ribosomal site of protein synthesis during translation. tRNA molecule has a 3' terminal site for the covalent linkage of a specific amino acid. The covalent linkage is catalyzed by an enzyme named aminoacyl tRNA synthetase. In addition, the tRNA molecule includes a three base region named the anticodon, which may base pair to the corresponding three base codon region on the mRNA molecule, which is the template for the protein synthesis. Each type of tRNA molecule may be attached to only one type of amino acid, however, since the genetic code includes multiple codons that specify the same amino acid, tRNA molecules bearing different anticodons may carry the same amino acid. (Lodish H, Berk A, Matsudaira P, Kaiser C A, Krieger M, Scott M P, Zipursky S L, Darnell J. (2004). Molecular Biology of the Cell. WH Freeman: New York, N.Y. 5th ed).

tRNA molecules are made and processed in the cell nucleus by a process known as transcription, while its site of action is in the cytoplasm, when participating in protein synthesis, as mentioned above. Hence, tRNA molecules translocate (move) between different subcellular locations. The dynamic movement and steady state accumulation of tRNAs in and between various subcellular locations may be dictated by the sensing of physiological states of the cell and may be regulated by mechanisms that are related to tRNA biosynthesis, function and turnover. Regulation of tRNA availability is central in the cellular response for the need of protein synthesis. Various cellular cues may dictate the function of tRNA by regulating the association of the tRNA with various cellular elements, such as, for example, association of tRNAs with amino-acyl-tRNA synthetases, association of tRNA with translation factors, association of tRNA with cytoplasmic polysomes, association of tRNA with ER-associated polysomes, and the like. In addition, alterations to the intracellular distribution of t-RNAs and sites of protein synthesis occur according to the onset of cellular programs such as cellular growth, division, differentiation, movement and cell-pathogen interactions. For example, viruses which generate localized foci of replication and assembly, termed viroplasms or viral factories, tailor the intracellular milieu to their needs, and may monopolize and concentrate the protein synthesis machinery in sites which differ significantly to those present in uninfected cells. (Castello, A., A. Quintas, et al. (2009), PLoS Pathog 5(8): e1000562; Katsafanas, G. C. and B. Moss (2007), Cell Host Microbe 2(4): 221-8; Qin, Q., C. Hastings, et al. (2009), J Virol 83(21): 11090-101; Smith, J. A., S. C. Schmechel, et al. (2006), J Virol 80(4): 2019-33).

It has previously been shown that in yeast, the tRNA retrograde process (the move/transport of tRNA from the cytoplasm to the nucleus), is energy-dependent, rapid, reversible, and may be responsive to nutrient availability. The re-export to the cytoplasm requires tRNA aminoacylation in the nucleus and probably the binding of eEF1A, which also is present in the nucleus (reviewed by Hopper A K, Pai D A, Engelke D R., FEBS Lett. 2010 Jan. 21; 584(2):310-7). Another publication (Shaheen H H, Horetsky R L, Kimball S R, Murthi A, Jefferson L S, Hopper A K. Proc Natl Acad Sci USA. 2007 May 22; 104(21):8845-50) has shown a retrograde tRNA transport in rat hepatoma cells upon amino acid starvation. Additional publication has shown that Lenti retroviruses use the tRNA retrograde cellular process to deliver their reverse-transcribed genome into the nucleus in non-dividing neuronal cells (Zaitvesa L., Mayers R., Fassati A. (2006), PLos Biol 4:e332).

Nevertheless, the retrograde transfer of tRNA to the nucleus has not been imaged in real time, while it is occurring, in viable cells. Moreover, a correlation between various cellular stress conditions and the changes (spatial and/or temporal) of tRNA subcellular localization have not been demonstrated in living cells. There is thus an ongoing need for methods that provide detection and measurement of the retrograde movement of tRNA in cells. There is further an ongoing need for methods that provide detection and measurement of the retrograde movement of tRNA in cells in real time. There is also a need for methods for detecting, measuring and/or assessing various cellular stress conditions in real time in viable cells, by tracking the subcellular tRNA localization and changes in said localization.

SUMMARY OF THE INVENTION

The present invention provides systems and methods for detection and assessment of tRNA localization in viable cells and for detection and assessment of changes in the tRNA localization. In some embodiments, the detection and assessment of the tRNA localization and changes in the tRNA localization are performed in real time. There are further provided methods and systems for the detection, measurement and/or assessment of various cellular stress conditions, by detecting subcellular localization and/or changes in the subcellular localization of tRNA, in viable cells. Such methods overcome problems and disadvantages associated with current strategies and methods and unexpectedly provide an efficient method for detecting, measuring and assessing various cellular stress conditions in living cells, by detecting tRNA subcellular localization. Such methods may be used for various applications, such as, for example, diagnostic methods, process-control methods, process-development methods, and the like. In some embodiments, the methods and systems for the detection, measurement and/or assessment of various cellular stress conditions, by detecting subcellular localization and/or changes in the subcellular localization of tRNA are performed in real time.

There is thus provided, according to some embodiments, a method for the quantitative assessment of cellular stress. There is further provided, in accordance with some embodiments a "stress index" which correlates between the tRNA subcellular localization and/or the spatial-temporal changes of the tRNA subcellular localization, and between a stress condition. The methods according to embodiments of the present invention may be utilized for numerous applications, such as, for example, but not limited to: identifying whether a cell is in stress condition; identifying the type of stress; quantifying the severity of the stress; monitoring cell growth (for example, by monitoring the exact timing of nutrient shortage in cell cultures); monitoring negative effects imposed by changes in growing conditions of the cells (such as, for example, pH, temperature, energy source level, and the like); monitoring initial stages of infection by various pathogens, such as, for example, viruses or *mycoplasma* or pathogenic bacteria or filamentous fungi; monitoring the effect of antibiotics on the translational machinery; monitor the effect of drugs on cells; providing predictive toxicology for drug development; providing process control for bio-manufacturing; providing high-throughput screening for drug discovery, and the like, or any combination thereof.

According to some embodiments, there is provided a method for detection of cellular stress in a cell, the method comprising introducing a labeled tRNA into the cell; detecting the subcellular localization of the tRNA over the course of a predetermined period of time, wherein the detection is based on a signal emitted from the labeled tRNA; and detecting a change in the subcellular localization of the labeled tRNA in the cell; wherein the change is indicative of stress in the cell. The subcellular localization may include nuclear localization, cytoplasmic localization, or both. In some embodiments, the increased subcellular nuclear localization of the tRNA is indicative of increased cellular stress. In some embodiments, a decreased subcellular cytoplasmic localization of the tRNA is indicative of increased cellular stress. The cytoplasmic localization may include intracellular organelles, endoplasmic reticulum (ER), stress granules, vacuoles, mitochondria, lysosomes, autophagosomes, or any combination thereof.

According to some embodiments, the fluorescently labeled tRNA may include Cy3-tRNA, Rho-110tRNA, Cy5-tRNA, Alexa-based fluorophore-tRNA, small organic fluorophore-tRNA, a fluorescent moiety-tRNA, a chemically modified tRNA such that the chemically modified tRNA is fluorescent, or any combination thereof.

In some embodiments, the detection may include imaging, biochemical assays, or both. Imaging may be performed by confocal microscopy, fluorescent microscopy, wide field microscopy, or any combination thereof. The biochemical assay may include fractionation, immunostaining, immunoblotting, chromatography, cross-linking or any combination thereof.

According to further embodiments, the stress may include heat shock stress, metabolite stress, pathogen infection stress, oxidative stress, toxic stress, radiation stress, ER stress, unfolded protein response (UPR) stress, any other cellular stress, or any combination thereof.

In some embodiments, the cell is selected from a primary cell, a tissue culture cell, a mammalian cell, yeast cell, an avian cell, a plant cell or another isolated cell type.

According to additional embodiments, the method may further include detecting a marker of a subcellular compartment. The marker may include a dye, an antibody, an antigen, a protein, an organelle, or any combination thereof.

According to additional embodiments, the method may further include comparing the subcellular localization of the labeled tRNA and the marker of the subcellular compartment.

In some embodiments, the method is qualitative, quantitative, or both.

In some embodiments, the method is performed in real time. In other embodiments, the method is performed on a fixated cell, using time lapse measurements on a series of cells.

According to some embodiments, the change in the subcellular localization of the labeled tRNA is a temporal change, a spatial change, or both.

According to additional embodiments, the tRNA is selected from a group consisting of mammalian tRNA, yeast tRNA, bacterial tRNA, avian tRNA, plant tRNA and derivatives and combinations thereof.

According to some embodiments there is provided a method for detection of anti-oxidant activity of a compound; the method comprising: introducing a labeled tRNA to a cell; detecting the subcellular localization of the tRNA; and detecting a change in the subcellular localization of the labeled tRNA in the cell after exposure of the cell to the compound, wherein the detection is based on the signal emitted from the labeled tRNA and wherein the change is indicative of the stress of the cell. The subcellular localization comprises nuclear localization, cytoplasmic localization, or both. In some embodiments, a decreased subcellular nuclear localization of the tRNA is indicative of increased anti-oxidant activity. In some embodiments, an increased subcellular cytoplasmic localization of the tRNA is indicative of increased anti-oxidant activity. In other embodiments, the compound is a drug, a substance, a chemical moiety, a peptide, or any combination thereof.

According to some embodiments, there is provided a method for generating a stress index of a cell, the method comprising detecting a spatial-temporal change in subcellular localization of a labeled tRNA in the cell; and computing the stress index based on the degree of the spatial-temporal changes in the subcellular localization of the labeled tRNA. In some embodiments, the stress index is a numeric stress index. In some embodiments, the cellular stress may include heat shock stress, metabolite stress, pathogen infection stress, oxidative stress, toxic stress, radiation stress, ER stress, unfolded protein response (UPR) stress, or any combination thereof. The subcellular localization may include nuclear localization, cytoplasmic localization, or both. The labeled tRNA may include fluorescently labeled tRNA. The tRNA may be selected from a group consisting of mammalian tRNA, yeast tRNA, bacterial tRNA, avian tRNA, plant tRNA and derivatives and combinations thereof. In some embodiments, detecting may include imaging methods, biochemical method, or both. In some embodiments, the method is performed in real time. In some embodiments, the method is performed on a fixated cell.

In some embodiments, image processing analysis may be used to compute the stress index and provide an output to the user. In some embodiments, the output is per cell. In some embodiments, the output is an average of more than one cell in a culture.

In some embodiments, cells may be analyzed by a high-throughput cell analyzer on a multi well plate and the stress index may be computed for each well, or any selection of wells.

In some embodiments, the cell stress index may be determined following one or more treatments to the cells. The one or more treatments may include, for example, but not limited to: addition of a substance, such as, for example, a chemical molecule, addition of drug, addition of a drug candidate, and the like. The stress index may be used to determine the effect of the treatment on the cell, for example, during drug discovery or drug development program.

In some embodiments, the index has a numeric value is in the range of 1 to 10. In some embodiments, an increase in the index is indicative of an increase in cellular stress.

According to additional embodiments, the method may further include detecting a marker of a subcellular compartment. In some embodiments, the computing of the stress index may further include correlating the subcellular localization of the tRNA and the marker of a subcellular compartment. In some embodiments, the method further includes generating a cell-state vector.

According to some embodiments there is provided a system for generating a stress index of a living cell, the system comprises a living cell having a labeled tRNA introduced thereto; a detection device adapted to detect and measure spatial-temporal changes in subcellular localization of the labeled tRNA; and a processing logic adapted to compute the stress index based on the spatial-temporal changes in subcellular localization of the labeled tRNA.

According to some embodiments, the stress index generated by the system is a numeric stress index. In some embodiments, the stress index generated by the system is indicative of a degree and/or type of a cellular stress. The cellular stress may include heat shock stress, metabolite stress, pathogen infection stress, oxidative stress, toxic stress, radiation stress, ER stress, unfolded protein response (UPR) stress, or any combination thereof. The subcellular localization comprises nuclear localization, cytoplasmic localization, or both. In some embodiments, the labeled tRNA comprises fluorescently labeled tRNA. The tRNA may be selected from a group consisting of mammalian tRNA, yeast tRNA, bacterial tRNA, avian tRNA, plant tRNA and derivatives and combinations thereof. In some embodiments, the detection device comprises an imaging device. The imaging device may include a fluorescence microscope, a confocal microscope, or another suitable detection device.

In some embodiments, the index generated by the system has a numeric value in the range of 1 to 10. In some embodiments, an increase in the index is indicative of an increase in cellular stress.

According to some embodiments, the detection device is further adapted to detect a marker of a subcellular compartment.

According to further embodiments, the detection of the spatial-temporal changes is performed in real time. In other embodiments, the detection of the spatial-temporal changes is performed on fixated cells, using time lapse studies on multiple individual cells.

According to some embodiments, there is provided a system for the detection of stress in a living cell, in real time, the system comprises: a living cell having a labeled tRNA introduced thereto; a detection device adapted to detect and/or measure changes in subcellular localization of the labeled tRNA, in real time; and an enclosed (incubator-like) chamber adapted to provide the cell controlled growing conditions.

According to some embodiments, the detection device comprises an imaging device. The imaging device comprises a camera, a confocal microscope, a fluorescence microscope, a plate reader, a fast cell sorter, other imaging devices, or another imaging device.

According to some embodiments, the subcellular localization comprises nuclear localization, cytoplasmic localization, or both. The cytoplasmic localization may include, for example, mitochondrial localization, ER localization, specialized compartments, such as dendritic spines in neurons, fibroblasts projections, or any other subcompartment of interest in the cell or another cytoplasmic localization. In some embodiments, an increased subcellular nuclear localization of the tRNA is indicative of increased cellular stress.

According to further embodiments, the labeled tRNA comprises fluorescently labeled tRNA. The fluorescently labeled tRNA comprises Cy3-tRNA, Rho-110-tRNA, Cy5-tRNA, small organic fluorophore-tRNA a fluorescent moiety-tRNA, a chemically modified tRNA, or any combination thereof. The tRNA may be selected from a group consisting of: mammalian tRNA, yeast tRNA, bacterial tRNA, avian tRNA, plant tRNA, mitochondrial tRNA, chloroplast tRNA, derivatives and combinations thereof.

According to further embodiments, the stress comprises: heat shock stress, metabolite stress, pathogen infection stress, oxidative stress, toxic stress, radiation stress, ER stress, unfolded protein response (UPR) stress, any other type of stress or any combination thereof.

According to additional embodiments, the cell is selected from primary cell, tissue culture cell, mammalian cell, yeast cell, avian cell, plant cell or another eukaryotic cell type.

According to further embodiments, the detection device is further adapted to detect a marker of a subcellular compartment. The marker comprises: a dye, an antibody, an antigen, a protein, an organelle, or any combination thereof.

In some embodiments, the changes in the tRNA subcellular localization may include a temporal change, a spatial change, or both.

According to further embodiments, the controlled growing conditions comprises: pH, temperature, humidity, $CO_2$ levels, media type, dissolved oxygen, mixing levels, illumination, any other condition or any combination thereof.

In addition to the exemplary aspects and embodiments described above, further aspects and embodiments will become apparent by reference to the figures and by study of the following detailed description.

BRIEF DESCRIPTION OF THE FIGURES

Some non-limiting exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. For convenience or clarity, some elements or structures are not shown or shown only partially and/or with different perspective or from different point of views. The figures are listed below.

DETAILED DESCRIPTION OF PREFERRED EMBODIMENTS

Figure 1:
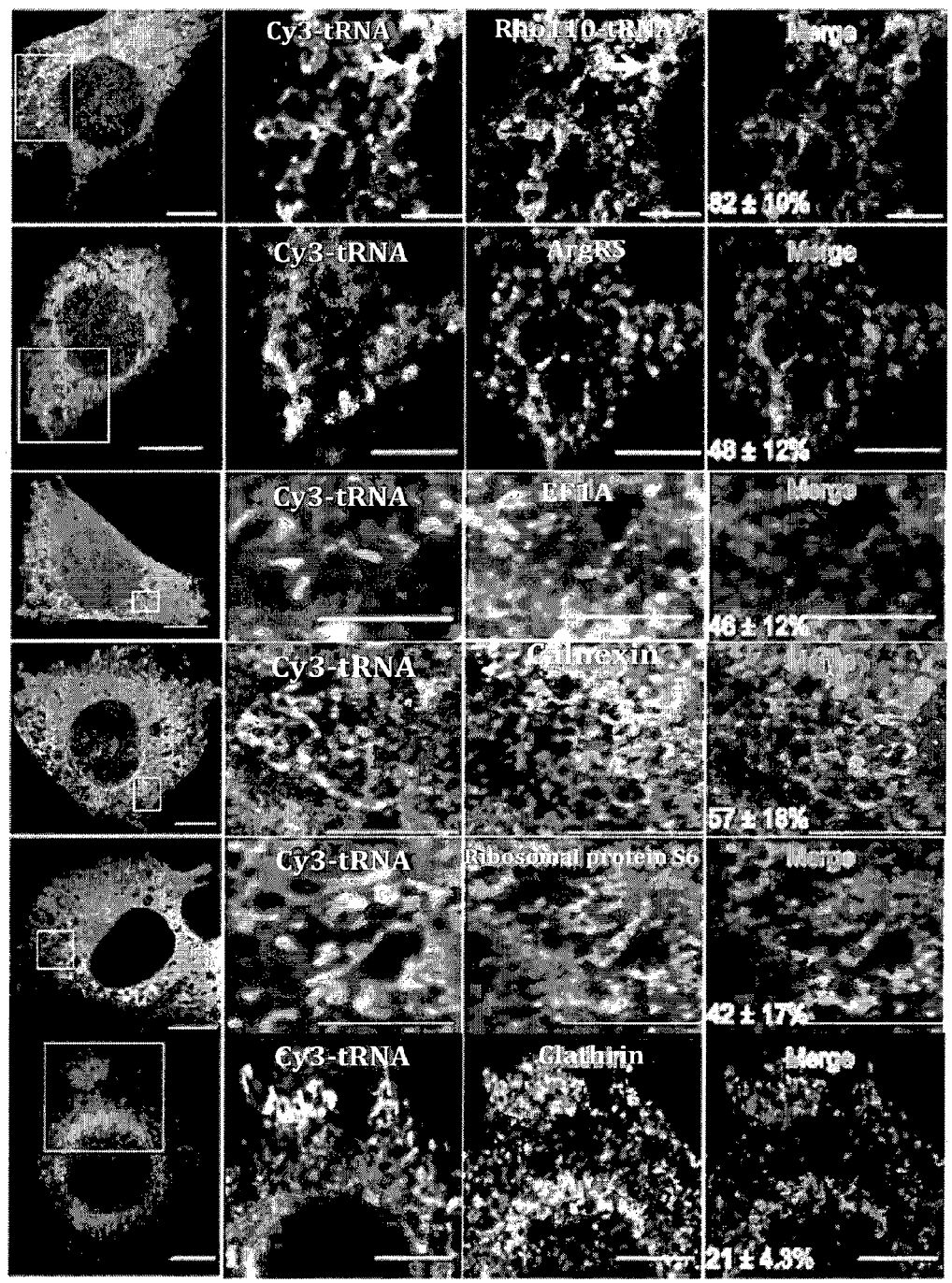
FIG. 1 depicts pictures of cells transfected with Cy3-labeled yeast tRNA showing partial co-localization with various components of the protein synthesis machinery.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

As used herein, the term "tRNA" refers to transfer ribonucleic acid. The tRNA may be an endogenous tRNA (that is, a natural (native) occurring tRNA, synthesized within a cell, whose template is contained in the cell genome). The tRNA may be an exogenous tRNA. The exogenous tRNA may be introduced into the cell, as detailed below. The exogenous tRNA may be of any origin, such as, for example, mammalian tRNA, yeast tRNA, bacterial tRNA, avian tRNA, plant tRNA, and the like. In some embodiments the tRNA may be transcribed from a natural or modified DNA sequence, and may be further modified biochemically or in other ways. In some embodiments, the tRNA may be modified, covalently or transiently. In some embodiments, the tRNA may be labeled. In some embodiments, the tRNA purified and labeled in vitro (as detailed below), and then introduced into the cell, as further detailed below. In some embodiments, the tRNA is transcribed within the tested cell, based on an artificial template introduced into the cell.

The term "mRNA" is used herein to describe a ribonucleotide sequence that transfers genetic information to ribosomes, where it serves as a template for protein synthesis. Ribonucleotide sequences are polymers of ribonucleic acids, and are constituents of all living cells and many viruses. They consist of a long, usually single-stranded chain of alternating phosphate and ribose units with the bases adenine, guanine, cytosine, and uracil bonded to the ribose. The structure and base sequence of RNA are determinants of protein synthesis and the transmission of genetic information.

As used herein, the term "cell" refers to a eukaryotic cell. Suitable cells can be, for example, but not limited to, of mammalian, avian, insect, yeast, filamentous fungi or plant origin. Non-limiting examples of mammalian cells include human, bovine, ovine, porcine, murine, and rabbit cells. The cell may be a primary cell or a cell line. In some embodiments, the cell can be an embryonic cell, bone marrow stem cell, or other progenitor cell. In some embodiments, the cell is a somatic cell, which can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a neuron, astrocyte, oligodendrocyte or microglial cell), or pathogen-infected cell (e.g., those infected by *mycoplasma*, bacteria, viruses, virusoids, parasites, or prions).

As used herein, the terms "cellular stress" and "stress" may interchangeably be used and are directed to a situation in which in response to a condition which impose on a cell pressure or demand, the cell acts by changing at least one of its normal function(s). Cells may respond to cellular stress in a variety of ways ranging from activation of intracellular pathways that promote survival to activating programmed cell death that eliminates a damaged cell. The initial response of the cell to a stress condition is directed in helping the cell defend against and recover from the condition induced by the stress. There are numerous types of stress and the response a cell may elicit to deal with the stress condition may depend on the type and level of the stress. Exemplary stress conditions, include, but are not limited to: temperature stress, which is induced by changes in temperature (for example, heat shock stress is induced by elevated temperatures); metabolite stress, induced by, for example, shortage/access of various metabolites in the environment and/or in the cell; pathogen infection stress, induced by, for example, infection of the cell; oxidative stress, induced by, for example, access of free radicals in the environment and/or within the cell; toxic stress, induced by, for example, various toxins, drugs and/or chemicals in the environment and/or within the cell; radiation stress, induced by various radiation sources, such as, for example, ionizing radiation; ER stress, which can be caused by accumulation of unfolded protein aggregates (unfolded protein response, UPR); and the like.

As used herein, the terms "subcellular localization", "subcellular region" and "subcellular compartment" refer to any defined part of the cell that may be distinguished by various means (such as, for example, by visual means) from other regions of the cell. In some examples, a subcellular region may be a restricted area within a cell. In some embodiments, a subcellular region may include an organelle. Non limiting examples of subcellular localization include, for example, but not limited to: nucleus, nucleolus, cytosol, mitochondria, endoplasmic reticulum (ER), chloroplasts, membranes, dendritic spines, and the like.

As used herein, the term "introducing" refers to the transfer of molecules, such as, tRNAs, various nucleic acids, translation factors, amino acids, and the like, from outside a host cell or subcellular compartment to inside a cell or subcellular compartment. The molecules can be "introduced" into a cell or subcellular compartment by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a host cell or subcellular compartment include, but are not limited to: heat shock, calcium phosphate transfection, electroporation, lipofection, transfection reagent(s), viral-mediated transfer, and the like.

As used herein, the term "transfection" refers to introduction of a nucleic acid into the interior of a membrane-enclosed space of a living cell, including introduction of the molecule into the cytosol of a cell, the nucleus of a cell, an interior space of a mitochondria, endoplasmic reticulum (ER), chloroplast, and the like. The nucleic acid may be, for example, a modified nucleic acid that may be in the form of DNA, RNA, or tRNA. The DNA, RNA, or tRNA is in some embodiments associated with one or more molecules, such as, for example, a protein, a dye, a labeling reagent, a tag, and the like. In another embodiment, the nucleic acid is incorporated into a vector, such as, for example, an expression vector. Each possibility represents a separate embodiment of the present invention.

As used herein, the term "infection" means the introduction of a molecule such as, for example a nucleic acid or a modified nucleic acid, such as DNA, RNA, tRNA into a recipient cell, subcellular compartment, or organism, by means of a virus. Viral infection of a host cell is a technique that is well established in the art and is described in a number of laboratory texts and manuals such as Sambrook et al., Molecular Cloning: A Laboratory Manual, Vol. 1-3, Cold Spring Harbor Laboratory, Cold Spring Harbor, N.Y., 2001.

As used herein, the term "label", is directed to a molecule that can be directly (i.e., a primary label) or indirectly (i.e., a secondary label) detected. A label can be visualized and/or measured and/or otherwise identified so that its presence, absence, or a parameter or characteristic thereof can be measured and/or determined.

As used herein, the terms "fluorescent label" and "fluorophore" refers to any molecule that can be detected via its inherent fluorescent properties, which include fluorescence detectable upon excitation. Suitable fluorescent labels include, but are not limited to, fluorescein, rhodamine, tetramethylrhodamine, eosin, erythrosin, coumarin, methylcoumarins, pyrene, Malachite green, stilbene, Lucifer Yellow, Cascade Blue, Texas Red, IAEDANS, EDANS, BODIPY FL, LC Red 640, Cy3, Cy5, Cy5.5, Alexa, LC Red 705 and Oregon green, as well as to fluorescent derivatives thereof. Suitable optical dyes are described in The Tenth Edition of Haugland, R P. The Handbook: A Guide to Fluorescent Probes and Labeling Technologies. 10th. Invitrogen/Molecular Probes; Carlsbad, Calif.: 2005, hereby incorporated by reference. Additional labels include but are not limit to fluorescent proteins, such as green fluorescent protein (GFP), yellow fluorescent protein (YFP), blue fluorescent protein (BFP), cyan fluorescent protein (CFP), quantum dots, FlAsH, ReHaSH, and the like.

As used herein, the term "FRET" ("fluorescence resonance energy transfer") refers to physical phenomenon involving a donor fluorophore and a matching acceptor fluorophore selected so that the emission spectrum of the donor overlaps the excitation spectrum of the acceptor. When donor and acceptor are in close proximity (usually less than 10 nm), excitation of the donor will cause excitation of and emission from the acceptor, as some of the energy passes from donor to acceptor via a quantum coupling effect. Thus, a FRET signal serves as a proximity gauge of the donor and acceptor; only when they are within close proximity is a signal generated (Ha, T., Methods 25, 78-86 (2001), review; De Angelis, D. A., Physiol. Genomics 1999, 31; 1(2): 93-9; Selvin, P. R., Nat. Struct. Biol. 2000 September; 7(9):730-4; Kenworthy, A. K., Methods. 2001 July; 24(3):289-96).

As used herein, "tags" can refer to any label known in the art, which can be detected either directly or indirectly.

As used herein, the term "in real time" relates to a situation where an action is being performed as an event occurs.

According to some embodiments of the present invention, there are provided system and method for detection and assessment of tRNA subcellular localization in viable cells. In additional embodiments, there are provided systems and methods to detection, measurement and/or assessment of spatial and/or temporal changes in the subcellular localization of tRNA in living cells, in real time, as the changes occur. As detailed below, the tRNA may, in some embodiments be labeled and may, in some embodiments, be introduced into the cell. Thereafter, according to methods and systems of embodiments of the present invention, the subcellular localization of the labeled tRNA may be detected and/or measured.

In some embodiments, the detection and/or quantitation of the subcellular localization of the labeled tRNA and changes in its localization may be performed in living cells, preferably in real time, as the changes occur. A labeled tRNA introduced into the cells is recognized by the cell as an "authentic" tRNA and is biologically active in the transfected cell. The transfected tRNA is biologically active as can be demonstrated by various lines of evidence, such as, for example, demonstrating co-localization with amino-acyl tRNA synthetase, translation elongation factor 1A and ER-bound polysomes; cycloheximide and puromycin sensitivity of ER-localized FRET signal generated by co-transfection of Cy3- and Rho-labeled bulk tRNAs), as further shown below in Example 1.

Additionally, without wishing to be bound to theory or mechanism, there are various cellular pathways to turnover and/or change the localization of damaged and/or normal tRNAs under various cellular conditions, such as, for example, cellular stress. For example, nuclear accumulation of cytoplasmic tRNA under various stress conditions may be used to separate tRNAs from the translational machinery under conditions which are unfavorable for protein synthesis. It is also possible that nuclear sequestration of tRNA is designed to serves a proofreading function to assure that only functional tRNAs molecules meet the protein synthesis machinery. Hence, in accordance with some embodiments, there are provided methods and systems for the detection, measurement and/or assessment of various cellular stress conditions, by detecting and/or measuring subcellular localization and/or changes in the subcellular localization of tRNA. There are further provided methods and systems for the detection, measurement and/or assessment of various cellular stress conditions, by detecting and/or measuring subcellular localization and/or changes in the subcellular localization of tRNA, preferably in real time, in viable cells. Such changes may include, for example, nuclear accumulation of cytoplasmic tRNA. As detailed below, the tRNA may, in some embodiments be synthesized or purified and labeled in vitro (not within the cell) and may then be introduced into the cell.

Additionally, there is further provided, in accordance with some embodiments a "stress index" which is indicative to and correlates with the degree and/or type of a stress encountered by a cell. The stress index is measured or calculated by correlating between various parameters, such as the tRNA subcellular localization and/or the spatial-temporal changes of the tRNA subcellular localization, and between a stress condition. In some embodiments, the stress index is a numeric index.

According to some embodiments, labeled tRNAs may be introduced into intact cells. The tRNA may be of any origin, such as, mammalian tRNA, yeast tRNA, bacterial tRNA, avian tRNA, plant tRNA, and the like. This can be accomplished through a variety of methods that have been previously established such as encapsulation of tRNA into liposomes or vesicles capable of fusion with cells. Fusion introduces the liposome or vesicle interior solution containing the tRNA into the cell. Alternatively, some cells will actively incorporate liposomes into their interior cytoplasm through endocytosis. The labeled tRNAs can also be introduced through the process of cationic detergent mediated lipofection (Felgner et al., Proc. Natl. Acad. Sci. USA 84:7413-17, 1987), or injected into large cells such as oocytes.

Additional methods for introduction of tRNA into a target cell are well known in the art. Such methods include, for example, the use of RNAiFect™ from Qiagen of Valencia, Calif. (Sako et. al., Nucleic Acids Symp Ser, 50:239-240, 2006) and electroporation. According to Sako et al, transfection of tRNA molecules, engineered to carry an anticodon for one of the natural stop codons (CUA, UUA, UCA) into A549 cells using the transfection agent RNAiFect™ (Qiagen, Hilden, Germany) is shown. The engineered tRNA were properly transfected and proved functional in a luciferase assay, where the luciferase gene included stop codons UGA, UAA, or UAG in place of the native Ser170 codon.

Additional methods for the introduction of nucleic acid molecules are described in Akhtar et al., Trends Cell Bio. 2, 139, 1992. WO 94/02595 describes general methods for introduction of enzymatic RNA molecules. These protocols can be utilized for the introduction of virtually any nucleic acid molecule. Nucleic acid molecules can be administered to cells by a variety of methods known to those familiar to the art, including, but not limited to, encapsulation in liposomes (WO 03057164; Malone, R. W. et al., 1989, Proc. Natl. Acad. Sci. USA. 86: 6077-6081; Glenn, J. S. et al., 1993, Methods Enzymol. 221: 327-339; Lu, D. et al., 1994, Cancer Gene Ther. 1: 245-252), by microinjection (Liu et al., 2005, Dev Growth Differ. 47(5):323-31), by iontophoresis (Sakamoto et al., 2004, Gene Ther. 11(3):317-24), or by incorporation into other vehicles, such as hydrogels, cyclodextrins, biodegradable nanocapsules, and bioadhesive microspheres.

In some embodiments, INTERFERin™ (Autogen Bioclear™, Wiltshire, UK) may be used for tRNA transfection. INTERFERin™ has been successfully used for tRNA transfection.

U.S. Patent Application No. 2004/235175 discloses a method of inserting RNA into cells. In this method, cells are transfected with RNA using electroporation in order to achieve high transfection efficiency.

In another, non-limiting exemplary electroporation protocol, $3-40 \times 10^6$ cells, preferably growing at log phase, are harvested, counted and washed with cold 1×HeBS (Hepes-buffered saline). Cells are resuspended in 0.8 mL 1×HeBS containing the tRNA and incubated at room temperature for 15 minutes. An exemplary recipe for HeBS is 20 mM HEPES, 150 mM NaCl, pH 7.0-7.4. The tRNA/cell suspension is transferred to an electroporation cuvette and electroporated at an appropriate voltage, preferably at between 500-2000 µF capacitance. The time constant is recorded if desired, and the mixture is optionally incubated in the cuvette for about 10 minutes at room temperature, prior to returning the cells to culture media.

In another, non-limiting exemplary electroporation protocol successfully used for CHO-K1 cells, HEK cells, and rat hippocampal neurons (thus having utility for a large variety of cell types), tRNA is precipitated (either alone or as a coprecipitate with DNA) in ethanol and ammonium acetate at $-20°$ C. for at least 1 hour. The precipitated tRNA is pelleted, vacuum dried, and resuspended in $CO_2$-independent medium to the desired final concentration (4 µg/µl tRNA, either with our without 2.5 µg/µl carrier DNA, is typically appropriate) Immediately prior to electroporation, the media is replaced with $CO_2$-independent media, containing no glutamine, FBS or antibiotics. $CO_2$-independent media are available e.g. from Invitrogen-Gibco and include phenol red free media, Liebovitz's L15 Media (catalogue no. 11415-114), and catalogue nos. 18055-088; 18045-088, and 041-95180M. Approximately 5 µl of electroporation solution is added to the cells, followed by electrical pulse application. For CHO-K1 cells and HEK cells, four 120 V pulses of 50 ms duration are typically used, and for neurons, four 160 V pulses of 25 ms duration. The $CO_2$-independent media is immediately replaced with fresh Ham's F12 media for CHOK1 cells, DMEM for HEK cells, or neurobasal media for neurons, and cells are returned to the 37° C. incubator.

In another, non-limiting exemplary electroporation protocol, electrolyte-filled fused silica capillaries (30 cm long, 30-µm id., 375-µm od.) are used. The outlet end of the capillaries is tapered to an approximate outer tip diameter (typically 50 µm, depending on the size of the cell type used). Exemplary electrolytes useful in this method are those based on HEPES buffer. The tapered outlet end of the capillary is submerged in the buffer contained in the cell chamber, and the inlet end is placed in a buffer-filled vial. Both the capillary and the inlet vial buffer solutions contain the tRNA and/or any other components to be transfected. Cells are placed in a chamber on the microscope stage, and cell bathing medium (HEPES buffer) is electrically grounded. The capillary outlet is placed within 5 µm of the cell surface, and the DC high voltage power supply is connected.

In another, non-limiting exemplary electroporation protocol, cells are electroporated using a modified patch-clamp technique. Single cells under direct observation are indented with a microelectrode and electroporated using a current delivered from a simple voltage-clamp circuit (as described in detail in Rae J L and Levis R A, Single-cell electroporation, Pflugers Arch 443(4):664-70, 2002).

In another, non-limiting exemplary electroporation protocol successfully used for electroporation of DNA, but equally useful for tRNA, into individual neurons in cultures of organotypic brain slices (FIG. 4), micropipettes with a tip diameter of about 1-2 µm and with resistances of 10-20 MΩ are pulled from capillary glass with filament (available from Science Products, Hofheim, Germany, catalogue number GB150F-8P) on a Micropipette Puller (available from Sutter Instrument Company, Novato, USA catalogue number P-97). Micropipettes are mounted on a three-axis micromanipulator (Luigs and Neumann, Ratingen, Germany). A Millicell CM insert (Millipore, Billerica, Mass., USA) containing a brain slice is placed in a perfusion chamber on the stage of a Zeiss Axioplan™ microscope and continuously perfused with oxygenated physiological salt solution during electroporation. The overall time under perfusion is typically about 30 min. Slices are transferred back into the incubator, individual cell somata are identified, and a pipette tip is gently placed against the cell membrane. Voltage pulses are delivered between an electrode placed inside the micropipette in contact with the tRNA solution (cathode), and a ground electrode (anode) using an isolated voltage stimulator (available from WPI, Berlin, Germany, under the name HI-MED HG-203) controlled by a tetanizer (available from Sigmann Elektronik, Hueffenbart, Germany). To prevent the tip from clogging and dilution of the tRNA, a back-pressure (typically 2-10 mbar) is applied to the pipette. In an exemplary embodiment, a single train of 200 square pulses with a duration of 1 ms is applied, using a 4 ms delay with an amplitude of 10 V. The 1 ms pulses remove the negatively charged tRNA from the pipette by electrophoresis, driving electroporation. Typically, no voltage is applied during the delay of 4 ms between the pulses and thus there is no current flowing through the circuit.

Each method for introduction of tRNA or nucleic acid into a cell represents a separate embodiment of the present invention.

According to some embodiments, the tRNA may be labeled. In some embodiments, the labeled tRNA may be an endogenous tRNA, labeled within an intact cell. In some embodiments, the labeled tRNA may be an exogenous tRNA. The exogenous tRNA may of any origin, such as, for example, mammalian tRNA, avian tRNA, yeast tRNA, bacterial tRNA, plant tRNA, and the like.

According to some embodiments, labeling of native tRNA may be performed by various methods, such as, for example by fluorescent labeling of native tRNAs at dihydrouridine (D) positions with rhodamine derivatives or other fluorophores, that are resistant to bleaching.

According to some embodiments, an exogenous tRNA introduced into cells may be labeled. Methods for fluorophore labeling of tRNA are well known in the art and are described, for example, in U.S. Pat. No. 7,288,372 and U.S. Patent applications 2003/0219780 and 2003/0092031, which are incorporated herein by reference.

In another exemplary method, used for Met-tRNA (Jun S Y et al, Fluorescent labeling of cell-free synthesized proteins with fluorophore-conjugated methionylated tRNA derived from in vitro transcribed tRNA. J Microbiol Methods. 2008 June; 73(3):247-51) but suitable for any tRNA, 10 µl of 30 mM succinimidyl ester of fluorescent dye in dimethyl sulfoxide (DMSO) is added to 40 µl of the Met-tRNA-fMet-resuspended solution and incubated for 40 min on ice. The reaction is stopped by adding one-tenth volume of 2M sodium acetate, pH 5.0. Fluorophore-conjugated Met-tRNA-fMet is extracted repeatedly with an equal volume of acid phenol: chloroform (1:1, v/v; pH 5.0. Two and a half volumes of cold 95% (v/v) ethanol solution are added to the aqueous phase, and the mixture is allowed to stand at −70° C. for 1 h to precipitate fluorophore-conjugated Met-tRNA-fMet. The precipitated pellet is collected by micro-centrifugation at 14,000 rpm at 4° C. for 20 min, and then resuspended in an equal volume of diethyl pyrocarbonate (DEPC)-treated water to the original reaction volume. After alcohol precipitation, the precipitate is washed with 80% (v/v) ethanol solution, dried under vacuum, and resuspended in 20 µl of DEPC-treated water.

In another exemplary method, used for conjugation of BODIPY-FL to Met-tRNA (Olejnik J et al, N-terminal labeling of proteins using initiator tRNA. Methods. 2005 July; 36(3):252-60), but suitable for conjugation of BODIPY-FL to any tRNA, 1.0 $OD_{260}$ (1500 pmol) of methionyl-tRNA-fMet (tRNA-fMet [Sigma Chemicals, St. Louis, Mo.], aminoacylated with methionine) is dissolved in water (37.5 µl), followed by addition of 2.5 µl of 1N $NaHCO_3$ (final conc. 50 mM, pH 8.5), followed by 10 µl of 10 mM BODIPYFL-SSE solution (Molecular Probes, Eugene, Oreg.). The modification reaction is allowed to proceed for 10 min at 0° C. and quenched by the addition of 0.1 volume of 1M lysine. 0.1 volume of 3M NaOAc, pH 5.0, is added, and modified tRNA is precipitated with 3 volumes of ethanol, dissolved in 50 µl of water, and purified on a NAP-5 column (Amersham-Pharmacia, Piscataway, N.J.) to remove any free fluorescent reagent.

In general, tRNA molecules can be tagged while retaining their interaction with the aminoacyl synthetases as well as retaining their functionality with the ribosome. tRNAs have been tagged with fluorescein (Watson et al., 1995, Biochemistry. 34 (24): 7904-12), with tetra methyl rhodamine (TMR) (Jia et al., 1997, Proc Natl Acad Sci USA. 7932-6), and with proflavine and ethidium bromide.

In some embodiments, tRNA may be labeled with small organic dyes attached to the "shoulder" region of the tRNA, such as in positions 8 and 47 of E. Coli tRNAs, which have been often used for this purpose. One particular labeling method is attaching the label of choice to one or both of the dihydrouridines in the D-Loop of the tRNA. Most tRNAs have these dihydrouridine modifications, enabling a wide choice of labels, including rhodamines, which are very useful due to their low tendency to bleach and high signal strength. The most widely used dyes are FITC and TMR (excitation peaks at 550 nm and emission at 573 nm).

In other embodiments, a tRNA may be labeled with the donor fluorescent label. Other tRNA may be labeled with the acceptor fluorescent label. The labeled tRNA mixture is administered to the cells. FRET may occur when both tRNAs are co-localized.

According to some embodiments, any cell of any origin may be suitable for use by methods of the present invention. The cells may include primary cells, derived from any organisms or tissue. The cells may include cells lines, such as, for example, but not limited to: COS, HEK-293, BHK, CHO, TM4, CVI, VERO-76, HELA, MDCK, BRL 3A, NIH/3T3 cells, and the like. Additional cell lines are well known to those of ordinary skill in the art, and a wide variety of suitable cell lines are available from the American Type Culture Collection, 10801 University Boulevard, Manassas, Va. 20110-2209.

According to some embodiments, there is provided a method for the detection and/or measurement of subcellular localization of labeled tRNA in cells. The method includes introducing the cell with a labeled tRNA. Labeling of the tRNA and its introduction into the cells may include any of the exemplary methods described above, or any other suitable method known in the art or to be developed in the future. After introduction into the cells, the labeling signal may be detected and/or measured. Detection and/or measurements of the labeling signal may be performed in accordance with the labeling signal by any of the methods known in the art. For example, detection of a fluorescence labeled tRNA in the cell may be performed by fluorescent microscopy, confocal microscopy, electron microscopy, wide field microscopy, scanning microscopy, a plate reader, a fast cell sorter, and the like. Additionally or alternatively, detection of a labeled tRNA in the cell may be performed by non-microscope based methods known in the art, such as, for example, cell fractionation, Western blotting and SDS-PAGE, immunoassay, immunostaining, chromatography, or any other methods of cell-biochemistry known in the art. In some embodiments, additional markers for cellular compartments or organelles that may be detected and/or measured by the methods used to detect/measure the tRNA may also be used in order to more clearly identify and distinguish the subcellular localization of the labeled tRNA. In some embodiments, the method is quantitative as it allows the measurement of the amount, concentration, intensity of the labeled tRNA in various subcellular compartments.

In some embodiments, there is provided a method for the detection and/or measurement of subcellular localization of labeled tRNA in cells, wherein the tRNA is an endogenous tRNA and is labeled within the cell.

According to other embodiments, a real time detection of tRNA in living cells may be performed. The real time detection of tRNA may be performed on living cells by identifying, tracking and/or measuring labeled tRNA molecules in the cells and at various subcellular compartments within the cells.

Accordingly, there is thus provided a method for the detection of tRNA in living cells, in real time, the method includes introducing one or more labeled tRNAs to the cells and detecting, measuring and/or quantifying the presence of the tRNA in the cells by using a live cell imaging system.

In one embodiment, the real time detection of tRNA in living cells is performed using live cell imaging system. The live cell imaging system may include an imaging device adapted to detect, measure and/or quantify the labeling signal in the cells and an incubator-like chamber adapted to maintain the cells in favorable conditions. An exemplary system is based on an imaging system that includes a spinning disk confocal microscope (an inverted Zeiss Axiovert 200M, coupled to a CSU-22 Yokogowa spinning disk confocal head and a CCD camera). The imaging device is endowed with an incubator-like chamber that is adapted to provide adequate growing conditions, such as, for example, pH, temperature, humidity, growing medium, dissolved oxygen, illumination, ventilation, $CO_2$ levels, and the like, to allow the monitoring of living cells over time, without affecting the growing conditions of the cells.

Accordingly, there is thus further provided a system for the real time detection of labeled tRNA in living cells, the system includes a detection device adapted to detect and/or measure the labeling signal of the tRNA, and an incubator-like chamber adapted to provide the cells with adequate growing conditions, such as, for example, but not limited to: pH, temperature, humidity, CO2 levels, medium type, oxygen saturation, illumination, ventilation, and the like, or any combination thereof.

In some embodiments, various subcellular compartments may also be labeled in living cells. The labeling of subcellular compartments may be performed, for example, by labeling of cellular organelles. The labeling of organelles may include the use of, for example, expression of genetically encoded fluorescent-protein-organelle-marker-fusion-constructs that are specifically expressed in specific organelles. An exemplary fluorescent-protein-organelle-marker-fusion-construct is a calnexin-GFP, which is specifically expressed in the endoplasmic reticulum (ER). In some embodiments, the labeling of various subcellular locations in living cells may include the use of specific fluorescent markers. For example, several of intracellular compartments may be accessible through labeling with various fluorescent compounds, such as, for example, Hoechst for nuclear labeling; internalized ligands that may be used to label the endosomal-lysosomal compartments, lipid dyes to label membranes, and the like.

According to some embodiments, a simultaneous detection of the labeled tRNA and subcellular locations may be performed. In such simultaneous detection, the subcellular location of the tRNA may be instantly recognized from the co-localization of the labeling signal of the tRNA and the labeled subcellular location. Co-localization of signals may be performed by any of the methods known in the art, including imaging methods, microscopy based methods, biochemical methods, and the like.

According to some embodiments, the detection of the labeled tRNA may further include measurements/quantitation of the labeled tRNA. The measurement may include quantitavely measuring and assessing the amount, intensity, concentration, and/or distribution pattern of the tRNA, as well as changes in any of those parameters.

According to some embodiments, and as detailed below, in response to various cellular stress cues, there are detectable changes in the subcellular localization of labeled tRNA. For example, in response to toxin stress (such as, for example, a stress induced by puromycin), there is a marked accumulation of tRNA in the nucleus of cells. Likewise, in another example, in response to pathogen induced stress (such as, for example, a stress induced by infection with Ibaraki virus), there is a marked accumulation of tRNA in virally induced structures (termed viroplasms) as well as in the nucleus of the cells. Hence, spatial changes in labeled tRNA subcellular localization can be observed in response to cellular stress. Again, without wishing to be bound to theory or mechanism, spatial changes in tRNA subcellular localization may be used to separate tRNAs from the translational machinery under conditions which are unfavorable for protein synthesis. It is also possible that nuclear sequestration of tRNA under stress condition is designed to serves a proofreading function to assure that only functional tRNAs molecules meet the protein synthesis machinery.

In additional embodiments, various stress markers, adapted for live cell microscopy, may also be used in order to demonstrate a correlation between various stress conditions and alterations in tRNA subcellular localization. Exemplary stress markers include such markers as, but not limited to: dyes, such as mitotracker, whose cellular retention is dependent on mitochondrial membrane potential (and thus mitochondrial function); dyes whose cellular penetration is dependent on loss of membrane impermeability; cell morphology; subcellular morphology, such as, for example, nuclear morphology; measurement of the kinetics internalization, recycling or lysosomal accumulation of dyes entering through the endocytic pathway; intracellular distribution of markers of lysosomes and autophagosomes; intracellular distribution of markers of stress granules; markers which indicate the structural integrity and dynamics of intracellular organelles such as the Golgi compartment (markedly altered in apoptosis and other pathological conditions). The detection of such stress markers in living cells, in addition to the detection of the labeled tRNA in living cells allows the enhanced assessment, preferably in real time, of the correlation between the type/severity of the stress and the subcellular localization of the tRNA. Additionally, subcellular changes in tRNA localization in non-mammalian cells (such as, for example, plant cells, yeast cells) may also be used for the detection and assessment of cellular stress. For example, t-RNA localization to the vacuole in non-mammalian cells (plant and fungi) may also be used as a marker of various cellular stresses.

According to some embodiments, there is thus provided a method for the detection of stress in cells, the method comprising detecting the subcellular localization of labeled tRNA in cells, wherein the spatial-temporal changes of the subcellular localization of the tRNA are indicative of the type and/or severity of the cellular stress. In some embodiments, the method is performed in live cells in real time by using the live cell imaging system as described herein. In some embodiments, the method may be performed on fixated cells that are fixated at any desired time point after a stress condition occurred/induced. In some embodiments, the methods further include the detection and/or analysis and/or measurement of various stress markers. In some embodiments, the labeled tRNA is introduced into the cell by any of the methods described herein. In some embodiments, the detection of the subcellular localization of the labeled tRNA in the cells is performed by imaging devices and methods, such as, for example, microscopy-based methods. In some embodiments, the detection of the subcellular localization of the labeled tRNA in the cells is performed by various biochemical methods well known in the art. In some embodiments, the detection of the subcellular localization of the labeled tRNA in the cells is performed by a combination of methods, such as, for example, microscopy-based methods, biochemical methods, and the like.

According to some embodiments, the method for the detection of cellular stress may be a qualitative method, quantitative method, or both. By qualitative method it is meant that the method may provide results that are indicative of a stress, without measuring and quantiating the degree and/or type of the stress. A qualitative method may provide a "yes-no" indication for a cellular stress. Bu quantitative method it is meant that the method may provide measurable results that may be quantified. A quantitative method may provide a more comprehensive result as to the degree and/or type of a cellular stress.

According to some embodiments, different types of cellular stress may be reflected in different spatial-temporal patterns of localization of the tRNA in the cells. For example, for toxin induced cellular stress, the spatial temporal changes in tRNA subcellular localization may be different from the spatial temporal changes in tRNA subcellular localization induced by viral stress.

According to some embodiments, there is provided a system for the detection of stress in a living cell, in real time, the system includes a living cell having a labeled tRNA introduced thereto, a detection device adapted to detect and/or measure changes in subcellular localization of the labeled tRNA, in real time, and an incubator-like chamber adapted to provide the cell controlled adequate growing conditions. The detection device may include, for example, an imaging device, such as, for example, confocal microscope, CCD camera, fluorescence microscope, a plate reader, a fast cell sorter, and the like. The adequate growing conditions provided by the incubator-like chamber include, for example, such conditions as, but not limited to: pH, temperature, humidity, $CO_2$ levels, medium type, oxygen saturation, illumination, ventilation, and the like.

According to some embodiments, there is further provided a stress index, which is indicative of the type and/or severity of a cellular stress, based on the spatial-temporal localization of the tRNA and the type and/or severity of a cellular stress. In some embodiments, the stress index may be used as a diagnostic indicator of a specific cellular state. In additional embodiments, the stress index may be a measure of the degree of the cellular stress and/or of the type of stress. In one embodiment, the stress index has a numerical value in the range of 1 to 10, wherein the higher the number, the higher the degree of stress and the less likely the cell is to survive the stress. In one embodiment, the stress index is a general stress index. In some embodiments, the stress index is a specific stress index, assigned to a specific type of stress, such as, for example, but not limited to: heat shock stress, metabolite stress, pathogen infection stress, oxidative stress, toxic stress, radiation stress, ER stress, unfolded protein response (UPR) stress, and the like. Different type of stress may induce different type of stress responses at different time frames. For example, with pathogen infection stress, the cell stress occurs in a time frame of days, depending on the replication cycle of the pathogen. For example, toxic stress induced by, for example, agents which perturb delicate regulatory cross points in the cells, such as, for example, ion homeostasis, tonicity, matrix attachment, pH, and the like, is sensed and reacted to in a time frame of seconds. For example, metabolite stress, such as, for example, nutrient deprivation, which leads to composite phenomena, may occur in an intermediate time scale of minutes to hours.

According to some embodiments, the stress index is a calculated (computed) index, based on the measured changes in the subcellular localization of the tRNA in the cells (spatial changes). Optionally, or additionally, the correlation index may also be based on the timing of said changes in the tRNA localization (temporal changes). For example, in response to heat shock stress (environment temperature is elevated to 39° C.), real time detection of tRNA in the cells, as performed according to embodiments of the present invention, show an increase of 20% in nuclear localization of tRNA after 25 minutes and is assigned a correlation index of 4. For example, in response to response to heat shock stress (environment temperature is elevated to 45° C.), real time detection of tRNA in the cells, as performed according to embodiments of the present invention, show an increase of 70% in nuclear localization of tRNA after 25 minutes and is assigned a correlation index of 8. In another example, in response to pathogen stress, induced by viral infection, after 2 days from infection, the real time detection of tRNA in the cells, as performed in accordance with embodiments of the present invention, show an increase of 25% in nuclear localization of tRNA and is assigned a correlation index of 5. In response to pathogen stress, induced by viral infection, after 4 days from infection, the real time detection of tRNA in the cells, as performed in accordance with embodiments of the present invention, show an increase of 85% in nuclear localization of tRNA and is assigned a correlation index of 9.

According to some embodiments, the stress index is a calculated (computed) index, based on the measured changes in the subcellular localization of the tRNA in the cells (spatial changes). Optionally, or additionally, the correlation index may also be based on the timing of said changes in the tRNA localization (temporal changes). Optionally or additionally, the correlation index may also be based on the correlation between the tRNA subcellular localization and the localization of various subcellular markers. In some embodiments, the correlation index may be calculated by various mathematical methods by creating a matrix integrating at least some of the various measured and/or calculated parameters. According to some embodiments, the correlation index is an integrated multi parameter index, wherein each parameter is individually assigned a numerical value, attributed to that parameter and the integrated correlation index is a representation of said individual numerical values. In some embodiments, the integrated correlation index may be calculated by use of various methods (such as, for example, various algorithms, mathematical models, fuzzy logic, a Bayesian network, a decision tree, a neural network, a radial base function, a linear regression model, a non-linear regression model, and the like), to provide a single numerical result. The numerical result may be, for example in the scale of 1-10, wherein the higher the value of the numerical result, the degree of stress is higher. In some embodiments, the integrated correlation index may be represented as a "matrix" index, wherein each parameter has an individual representative numerical value, which is represented in the "matrix index". An exemplary "matrix" correlation index may include a five digit index (in the scale of 1-9), wherein each digit is a numerical value of a different measured/calculated parameter. For example: the first digit is representative of the degree of co-localization of the tRNA with an ER marker; the second digit degree is representative of the co-localization with tRNA synthetase; the third digit is representative of the degree of co-localization with ribosomal protein S6; the fourth digit is representative of the degree of localization to the nucleus; the fifth digit is representative of the presence of intracellular accumulations, as defined by a high local variance to mean ratio of the fluorescence signal.

In some embodiments, the cells are grown in multi well plates, and the detection and analysis of the cells' stress and of the stress index may be performed by a high-throughput cell analyzing systems, such as, for example, "Opera" from Perkin Elmer, "IN cell analyzer" from GE healthcare and the like. In some embodiments, the stress index may be computed for each well (or selection of wells) having cells growing therein. In some embodiments, the stress index is calculated for a cell in a well.

According to further embodiments, there is provided a method for generating the stress index of a living cell, the method includes detecting a spatial-temporal change in subcellular localization of labeled tRNA in the cell and computing the stress index based on the degree of the spatial-temporal changes in the subcellular localization of the labeled tRNA. In some embodiments, the method may further include detecting and calculating a correlation between the tRNA subcellular localization and the subcellular localization of various subcellular markers. The labeled tRNA and its detection may be performed by any of the embodiments described herein. The computing of the stress index may be performed by various methods known in the art, such as, for example, but not limited to the use of various algorithms, mathematical models, fuzzy logic, a Bayesian network, a decision tree, a neural network, a radial base function, a linear regression model, a non-linear regression model, and the like, that may be used to quantitavely correlate between the spatial-temporal changes in the subcellular localization of the labeled tRNA and the degree/type of cellular stress. In some embodiments, the correlation index may be an integrated index. In some embodiments, the correlation index may be a matrix index, as detailed above.

According to some exemplary embodiments, the stress index may be calculated by computing a cell-stress vector of various values, which are indicative of the state of the cell. For example, the cell-stress vector may be computed as follows: the cells to be assayed are transfected with fluorescent tRNA probes as well as by one or more specific marker stains (for example, Calnexin for ER, DAPI for nucleus). The markers and fluorescent tRNA can be co-transfected to the same cells such that each cell is labeled with various both, or in parallel where separate sets of cells are each transfected with the fluorescent tRNA probes and with a subset of the required stains. The transfected tRNAs can be of a single label, for tRNA distribution measurements. Colocalization values between the tRNA distribution and each stain are computed as is well known in the art (Bolte, S., and Cordelieres, F. P. (2006) Journal of microscopy 224, 213-232). The results yield a vector of colocalization values that is indicative of the state of the cell—normal/stressed and optionally type of stress. Determination of the cell stress vector can be performed semi-manually by imaging the cells with an imaging device, such as a microscope, and using imaging software such as, for example, Slidebook™, Metamorph™, ImageJ or custom-developed protocols in Matlab™ to compute each value in the vector. Additionally or optionally, determination of the cell state vector can be performed automatically by performing the assay on an automated cell imager and using dedicated software to compute the cell state with respect to stress.

In accordance with additional embodiments, there is provided a system for the generation of a stress index of a living cell, the system includes a living cell transfected/infected with a labeled tRNA, a detection device adapted to detect and measure spatial-temporal changes in subcellular localization of the labeled tRNA, optionally, detecting various subcellular markers, and a processing logic adapted to compute the stress index based on the spatial-temporal changes in subcellular localization of the labeled tRNA. The labeled tRNA and its detection may be performed by any of the embodiments described herein. The processing logic may include any type of processing logic known in the art that may be used to compute the stress index based on various computing/calculating methods, such as, but not limited to: various algorithms, mathematical models, fuzzy logic, a Bayesian network, a decision tree, a neural network, a radial base function, a linear regression model, a non-linear regression model, and the like.

The methods disclosed in various embodiments herein provide several advantages over currently used methods for the detection of subcellular localization of tRNA in cells in general, and for the detection of changes in the subcellular localization in particular. For example, tRNA localization, assayed by using digoxiginin (DIG)-labeled DNA probes that are designed to hybridize with a specific tRNA type, is expensive, time consuming and requires high level of expertise, as it demands numerous steps for several probes preparation, cell fixation, pre-hybridization, hybridization, and staining with FITC-conjugated anti-DIG antibodies. For example, in order to gain information regarding retrograde tRNA transport in cells, using methods currently known in the art, there is a need to treat the cells with a drug to inhibit transcription of newly synthesized tRNA, which may impose further stress on the cells, and may thus induce artifact results. For example, currently used methods do not allow cellular stress assessment or its modulation or reversal, in real time in living cells.

According to some embodiments, the methods disclosed herein may be suitable for various diagnostic applications, wherein the subcellular localization of labeled tRNA as measured cells, preferably in real time, in living cells, is indicative of the type and/or severity of a the condition of the cell in general, and more specifically of a cellular stress.

In one embodiment, the methods disclosed herein may be used in the diagnosis of viral infection of cells. For example, by determining the localization of the labeled tRNA in the suspected cell, (as compared to the localization of the labeled tRNA in a control cell), an indication of the occurrence and of the severity of a viral infection may be determined (that is, if the cell is infected and the extent of virally induced phenomena).

In another embodiment, the methods disclosed herein may be used to assess the effects of various chemicals, such as, for example, drugs, on cells, in real time, in a dynamic system. In such a setting, the immediate effect of a drug on a cell may be detected, measured and/or quantitated in real time, by methods disclosed herein.

In additional embodiments, the methods disclosed herein may further be used for the detection of cellular stress even in conditions in which the source of stress is unknown. In such a setting, detection of spatial-temporal changes in tRNA localization in methods according to embodiments of the present invention may be indicative of a cellular stress, which may further allow identification of the stress and taking actions to avoid such stress.

In further embodiments, the methods disclosed herein may further be used for the real-time monitoring of various treatments and manipulations performed on living cells, aimed at reducing either cell stress in unwanted conditions (for example through therapeutic manipulations of cells suffering from neurodegenerative disorders), or inducing cell stress in conditions where it is desired (for example for the testing or screening of compounds aimed at generating stress to specific cellular populations, such as in the development of targeted anti-oncogenic therapy).

In another embodiment, the methods disclosed herein may further be used to monitor various cell culture conditions, and may further be used to optimize the growing conditions. For example, the methods disclosed herein may be used to monitor the exact timing of nutrient shortage in various cell cultures. In another example, the methods disclosed herein may be used to monitoring negative effects imposed by changes in the growing conditions (such as, for example, pH, temperature, energy source level). This may be particularly useful, for example, in the production of recombinant proteins produced by cell cultures. The ability to monitor and identify, in real time, the negative effects imposed by changes in the growing conditions may be used to increase yield and reduce production costs.

According to some embodiments, the methods and systems for identification and characterization of cellular stress, disclosed herein may further be used in various drug discovery platforms. According to some embodiments, and without wishing to be bound by any theory or mechanism, when a drug candidate molecule (such as, for example, a chemical compound) causes stress in a given cell, as detected by the methods disclosed herein, this may imply that the compound interacts with one or more intracellular pathways. Hence, this may serve as a basis for screening compound libraries for specific applications in various cell types and cultures. For example, for a specific panel of cells (primary cells, tissue culture cells, cell lines, and the like), the range of states of stress and the degree of the stress induced by a tested compound may provide valuable information regarding the mode of action of the tested compound in those cells. Additionally, the degree and type of stress induced by that compound may further provide valuable information regarding the toxicity of the tested compound to the tested cells. This is further demonstrated in Example 4, below.

According to further embodiments, an additional drug discovery field where the methods for detection of cellular stress as disclosed herein may be used is for the discovering and characterizing of compounds that reduce oxidative cell stress. Oxidative stress and reactive oxygen species (ROS) have been implicated in various disease states, such as Alzheimer's disease, Parkinson's disease, cancer, aging, Amyotrophic Lateral Sclerosis, and the like. Oxidative stress is imposed on cells as a result of an increase in oxidant generation, a decrease in antioxidant protection, and/or a failure to repair oxidative damage. Consequently, cell damage is induced by reactive oxygen species (ROS). ROS are either free radicals, reactive anions containing oxygen atoms, or molecules containing oxygen atoms that can either produce free radicals or are chemically activated by them. Under normal conditions, ROS are cleared from the cell by the action of enzymes, such as, for example, superoxide dismutase, catalase, or glutathione peroxidase. The main damage to cells results from the ROS-induced alteration of macromolecules such as polyunsaturated fatty acids in membrane lipids, essential proteins, and DNA. In order to use methods disclosed herein for the identification and characterization of molecules that induce cellular stress, tested cells, which can be primary cells or cell lines of interest exhibiting increased level of oxidative stress (such as SOD1 deficient cells) may be introduced with the fluorescent labeled tRNA probes, and then subjected to treatment by the test compound. In accordance with the methods and systems disclosed herein, changes in oxidative stress response are then measured. Cells showing significant reduction of oxidative stress indicate that the tested compound may have anti-oxidant activity. The method may be further applied for high throughput screening, by screening/assaying a panel of drug candidates on a large number of cell types. Such high-throughput assay may be performed, for example, by using a cell-based assay reader such as the IN cell analyzer (GE healthcare), Celigo (Cyntellect Inc), Opera (Perkin-Elmer), ImageXpress (Molecular Devices), and the like. Once activity is noted for a specific compound, the spectrum of stress responses across the various cell types tested may be further be used in elucidating the mechanism underlying the oxidative stress and anti-oxidant effects of that compound.

According to yet additional embodiments, an additional drug discovery field where the methods for identification of cellular stress as disclosed herein, may be used is for identifying and characterizing compounds having anti-infective activity, such as, for example, anti-viral, anti-bacterial, anti-parasites and/or anti-fungal compounds. As is well known in the art (and as also exemplified herein), infections of various sources may generate cell-stress, particularly when the infectious agent penetrate the cell-membrane and replicate inside the cell This is typical for viral infections but also can be implicated in various bacterial and parasitic infections. For example, Rickettsiae (causing for example Typhus) and *Chlamydia* (causing for example Trachoma and Urethritis) are obligatory intracellular bacteria. *Mycobacterium* (causing for example Tuberculosis) and *Brucella* (causing Brucellosis) are intracellular bacteria. Other examples include Fungi such as *Histoplasma* causing histoplasmosis and parasite such as *Toxoplasma Gondii* causing Toxoplasmosis. In order to use the methods and systems for identification of cellular stress as disclosed herein, for the identification and characterization of compounds having anti-infective activity, infected primary cells or cell lines of interest are transfected by the fluorescent labeled tRNA and subjected to a treatment by the test compound. Changes in the stress response are then measured, in accordance with the methods of the present disclosure. Cells showing significant reduction of stress, as determined by the methods and systems disclosed herein, indicate anti-infectious activity of the compound being assayed. The method may be further applied for high throughput screening, by screening/assaying a panel of drug candidates on a large number of cell types. Such high-throughput assay may be performed, for example, by using a cell-based assay reader such as the IN cell analyzer (GE healthcare), Celigo (Cyntellect Inc), Opera (Perkin-Elmer), ImageXpress (Molecular Devices), and the like. Once activity is noted for a specific compound, the spectrum of stress responses across the various cell types tested may be further be used in elucidating the mechanism underlying the anti-infectious effects of that compound.

According to some embodiments, the methods disclosed herein may further be used in various drug development platforms to test or predict potential adverse effects. As drugs are being developed an effort is being made to understand the interaction between the candidate drug and its respective target. However interactions with other targets, in different cells and tissues, may be hard to measure. Accordingly, the methods for identification of cellular stress disclosed herein may be used to identify adverse reactions and assist in predicting toxic effects, thereby shortening the drug development process, adding important information at an early development stage and reducing the risk of failing later clinical tests. In order to use the methods and systems for identification of cellular stress as disclosed herein, for drug development platforms, for the compound (drug) that is to be assayed, a panel of primary cells or cell lines of interest (heart, muscle, kidney, liver, CNS, and the like) is prepared. The cells are transfected by the fluorescent labeled tRNA probes and subjected to a treatment by the compound being assayed. Stress response is then measured, in accordance with the systems and methods disclosed herein. Cells showing significant stress indicate a potential toxic effect of the compound being assayed. The method may be further applied for high throughput screening, by screening/assaying a panel of drug candidates on a large number of cell types. Such high-throughput assay may be performed, for example, by using a cell-based assay reader such as the IN cell analyzer (GE healthcare), Celigo (Cyntellect Inc), Opera (Perkin-Elmer), ImageXpress (Molecular Devices), and the like. Once a toxic effect is suspected for a drug substance, the spectrum of stress responses across the cell lines may be of assistance in elucidating the mechanism underlying that effect.

According to some embodiments, the methods and systems for identification of cellular stress as disclosed herein may further be used in small and large scale biomanufacturing procedures. Due to the complexity of both the protein products and the cells that produce them, biomanufacturing is inherently fraught with difficulties, limitations, expenses and inconsistencies. During the cell culture phase of a production run, many factors are continuously monitored to ensure process performance, consistency, and health of the culture. While some parameters of the process are intrinsic, directly related to the state of the producing cells, many of the parameters, such as, for example, pH, dissolved oxygen, temperature, and the like, are extrinsic, and the relationship between the state of the producing cells and these parameters is open-ended. In particular, the health and well-being of the producing cells is of paramount importance. Deterioration of cell health can decrease the production rate, shorten the life-cycle of the production run, impact the final product quality (which may include modifications such as, correct folding, glycosylation, and the like) and even indicate dangerous situations such as viral infection of the cells in the reactor. Using the methods and systems for identification of cellular stress disclosed herein, a quality assurance method and system can be used. At predetermined time intervals (for example, hourly, daily) a sample of cells is pulled from the reactor, transfected by the fluorescent tRNAs and assayed for cell stress by any of the methods and systems disclosed herein. An indication of increase in stress conditions is a warning sign to identify the causes of the stress, thereby enabling either to remedy the situation or even shut the reactor down. This method can be further automatized using an automatic cell sampler attached to the reaction vessel, and an automated cell-based assay instrument to apply the fluorescent tRNAs reagents and measure the stress signal using pre-adapted imaging software. The result may further be fed into/provided to a quality control system of the biomanufacturing plant and standard statistical analyses can be used to provide a warning when increased cell stress is identified.

According to yet further embodiments, the methods and systems for identification of cellular stress as disclosed herein may also be used in various diagnostic applications, such as, for example, viral infections diagnostics. Viral infections are hard to identify. Some methods used today rely on RT-PCR, but this requires knowing the exact virus genome sequence before detecting its presence. There are thousands of known viruses and an unknown number of unknown virus sequences. Accordingly, there are provided system and method for identifying viral infections of cells, based on identification and characterization of cellular stress. In such a method, the cells to be assayed for viral infection are transfected with fluorescent labeled tRNAs and with additional one or more markers of intracellular compartments, such as, for example, a stain marking the ER. Localization of the labeled tRNAs and/or of the FRET signals is measured and the colocalization coefficient between the distribution and the ER stain is determined. The resulting data vector is then analyzed to determine, according to preset conditions, whether the cell has been infected by a virus. For example, ER-tRNA colocalization below a given threshold of T1 with total tRNA distribution concentrated around up to Nc centers results in a positive decision for that cell. For a given type of cell, nature of assay (single label assay/FRET assay) and additional parameters, various decision algorithms may be used. Additionally, such an assay can also be used to determine the number of cells in a given cell population that are suspected of having been infected by a virus. This can be achieved by coupling this assay to a high-throughput cell-assay imager. Accordingly, there is thus provided a system for diagnosing a viral infection, the system comprises an high-throughput cell-assay imager and a living cell having a labeled tRNA introduced thereto. Such a viral infection diagnostic method and system can be useful in numerous settings from medical diagnostics for human patients to quality control in biomanufacturing to applications in food safety and numerous additional applications.

When a range of values is recited, it is merely for convenience or brevity and includes all the possible sub-ranges as well as individual numerical values within that range. Any numeric value, unless otherwise specified, includes also practical close values enabling an embodiment or a method, and integral values do not exclude fractional values. A sub-range values and practical close values should be considered as specifically disclosed valued.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope. Terms in the claims that follow should be interpreted, without limiting, as characterized or described in the specification.

In the description and claims of the application, each of the words "comprise" "include" and "have", and forms thereof, are not necessarily limited to members in a list with which the words may be associated.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Transfected tRNA is Partially Co-Localized with Components of the Protein Synthesis Machinery Materials and Methods:

Chinese hamster ovary cells (CHO-Ki) were maintained in nutrient mixture F-12 (Ham) supplemented with 10% (v/v) fetal calf serum, 5 mM L-glutamine and antibiotics (all from Biological Industries).

Transfection—Cells were seeded in the day preceding the transfection ($1.5 \times 10^5$ cells, 12 mm coverslips, in 24-well plates). Transfection was with 3 µg of yeast labeled-bulk tRNA (Interferin™, polyplus-transfection, according to manufacture's instructions). For DNA transfection (pSuper-retro-GFP), $9 \times 10^4$ cells/well were transfected with 1 µg DNA (TransIT-LT1 transfection reagent, according to manufacture's protocol). The following day, cells were re-transfected with labeled tRNA as described above.

Quantitative image analysis—For quantitative analysis of spatial distribution of the labeled tRNA and additional cellular markers, the entire cell volume was imaged by spinning disk confocal microscopy (0.15 µm between planes of the z-stack) with a 100× lens and 1×1 "on chip binning" yielding a pixel size of 100×100 nm; and deconvolved with the constrained iterative algorithm of Slidebook™ which employs an experimentally measured point spread function (PSF). Images served as a basis for the calculation of the percentage of overlapping pixels (denominated CL, co-localization), or the cross correlation (maximum Pearson's cross correlation coefficient, calculated with ImageJ and denominated CCF throughout the text) amongst two signals.

Immuno-staining—CHO cells pre or post transfection, were fixed (4% PFA, 20 min, room temperature), permeabilized (0.5% triton-x, 10 min), extensively washed with PBS, blocked (PBS 1% BSA [PBS/BSA], 5% normal goat serum, 1 h) and stained. Primary antibodies employed (1:500 dilution, PBS/BSA, 4° C., overnight) included: arginyl-tRNA synthetase (Abcam), eEF-1A (Cell signaling), calnexin (Sigma), rpS6 (Cell Signaling) and anti-NS2 (this study). Secondary antibodies were AlexaFluor-488 IgG goat anti-rabbit and/or AlexaFluor-555 IgG goat anti-mouse (Invitrogen; 1:500 dilution, PBS/BSA, 2 h, room temperature). Coverslips were mounted with Fluoromount (Sigma). Images were acquired using a motorized spinning-disc confocal microscope (Yokogawa CSU-22 Confocal Head; Axiovert 200M, Zeiss) under the control of SlideBook™ (Intelligent Imaging Innovations). A 100× oil immersion objective lens was employed.

Figure 2A:
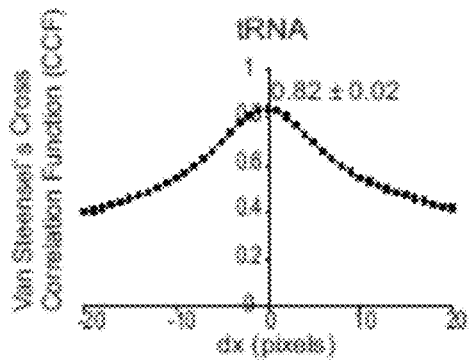
FIGS. 2A-G depict quantitative analysis of the confocal images presented in FIG. 1.
Figure 2B:
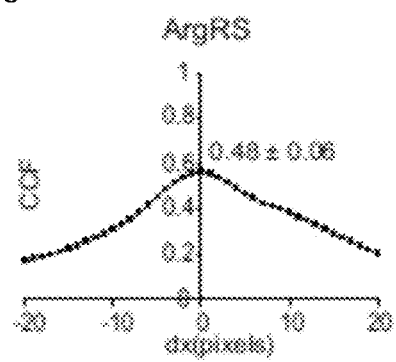
Figure 2C:
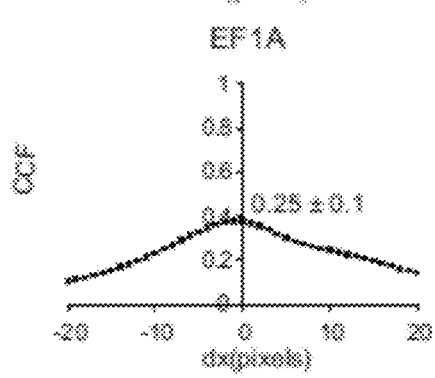
Figure 2D:
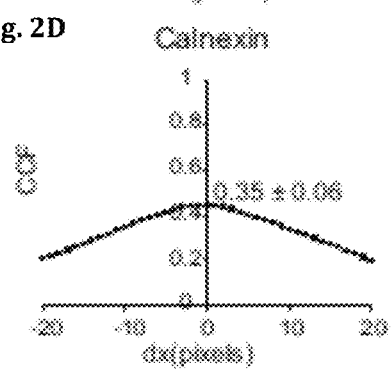
Figure 2E:
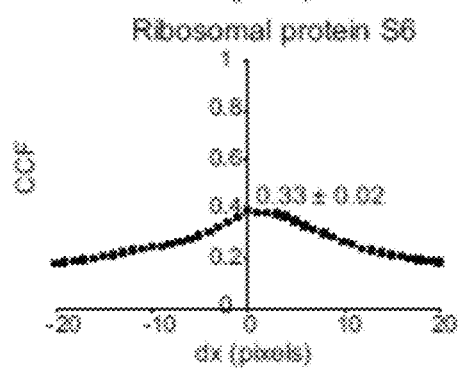
Figure 2F:
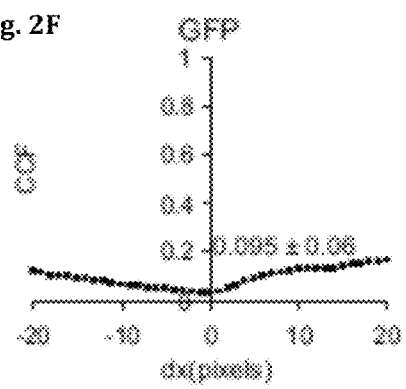
Figure 2G:
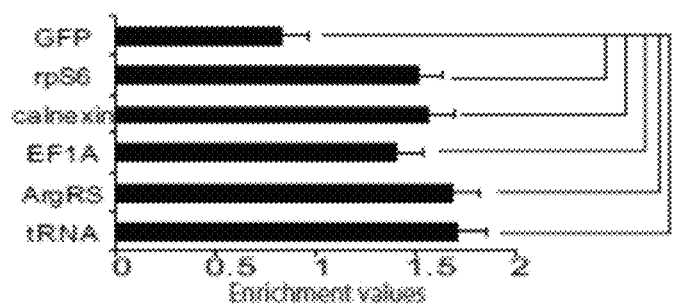

Results:

CHO cells were transfected with bulk Rho110-labeled and/or Cy3-labeled yeast tRNA, fixed 7 h post transfection and immuno-stained with antibodies against arginyl-tRNA synthetase (ArgRS), translation elongation factor 1A (eEF1A), Calnexin, Ribosomal Protein S6 (rpS6) or GFP. The results, presented in FIG. 1, shows partial degrees of fluorescence co-localization and cross-correlation measured with transfected Cy3-tRNA and endogenous immuno-stained arginyl-tRNA synthetase (ArgRS) (CL=48±12%; CCF=0.485±0.06), translation elongation factor 1A (eEF1A) (CL=46±12%; CCF=0.253±0.1), calnexin, used as a marker of the endoplasmic reticulum, a main site of protein synthesis (CL=57±18%; CCF=0.358±0.06), ribosomal protein S6 (rpS6), and clathrin (a non-ER marker of endomembranes). The results establish the accessibility of transfected fl-tRNA to sites associated with protein synthesis and support the notion of its functional participation in the act of mRNA translation in the transfected cells. Panels of FIG. 1 depict micrographs of single (middle) planes of representative cells imaged with a spinning disc confocal microscope and deconvolved employing the constrained iterative algorithm of Slidebook™. Second to the left hand column panels are micrographs of cells transfected with Cy3-tRNA. Second to the right column panels are micrographs of cells immunostained with the indicated antibodies. Right column panels are merged images of the corresponding second to the left and second to the right columns. Pictures of randomly selected cells (n=30 for each condition) were employed for the calculation of the co-localization and cross correlation of the fluorescent signals obtained with the different wavelengths. The Pearson's coefficient resulting from these calculations appears at the lower left hand corner of the merged images. Arrows show distinct co-localization sites. Bar is 5 μm. CCF values are presented in FIGS. 2A-F. The positive levels of CL (FIG. 1) and CCF (FIGS. 2A-F), are indicative of a partial co-localization with the different cellular factors and in accord with the various functional interactions of tRNA. The graphs shown in FIG. 2G depict the average ±SD of the enrichment factor of the co-localization of the different fluorescence signals. "Masks" of the fluorescence signals were generated through intensity-based segmentation (above the measured background). The enrichment factor was defined and calculated as the percentage of Cy3-tRNA signal overlapping with the different staining ('green signal"), divided by the percentage of the total cell volume occupied by the "green signal" (the expected random overlap).

Example 2

Puromycin Increases Nucleus-to-Cytoplasm tRNA Ratio

Materials and methods are as essentially as detailed above with respect to Example. 1.

Figure 3A:
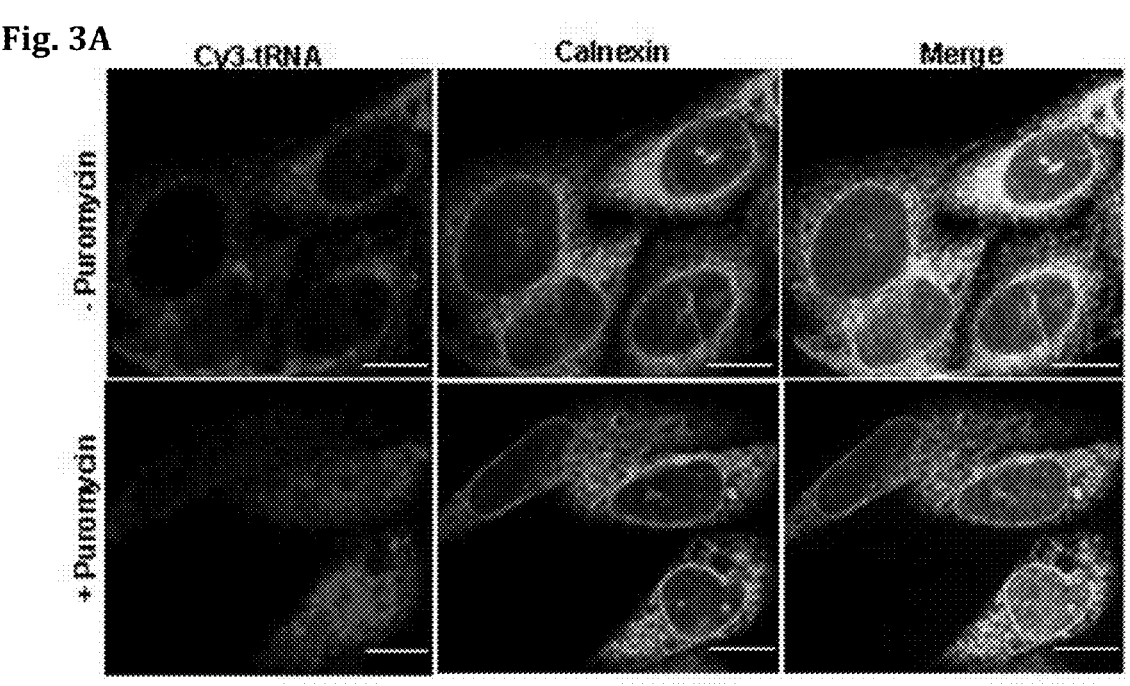
FIG. 3A depicts pictures of cells transfected with Cy3-labeled bulk tRNA in the presence or absence of puromycin treatment.
Figure 3B:
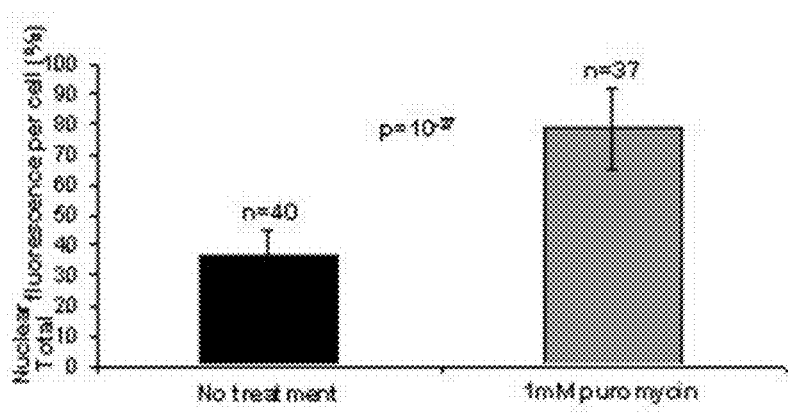
FIG. 3B depicts bar graphs of the percentage of tRNA signal in nucleus of cells, treated or non-treated with puromycin.

Results:

CHO cells that were transfected with Cy3-labeled yeast tRNA were treated with puromycin (7 h post transfection, 0.5 h, 1 mM); washed, fixed and stained against calnexin (marker of the ER) and DNA (Hoechst stain). The results, which are presented in FIG. 3, demonstrate the subcellular localization of tRNA in CHO cells treated or untreated with puromycin, known to inhibit transcription and thus impose cellular stress, by disrupting polysome disassembly. FIG. 3A depicts confocal micrographs of the median plane of representative cells under the condition indicted in the respective panels (Bar is 10 μm). The results show that in response to puromycin treatment, an increase in nuclear localization of labeled tRNA is observed. FIG. 3B is a bar graph which depicts the average percentage of the t-RNA signal that co-localizes with the Hoechst signal in cells treated (left hand bar) or untreated (right hand bar) with puromycin (N=~40 cells per condition, from 3 independent experiments). The results clearly demonstrate the increase in the nucleus to cytoplasm ration of the tRNA.

Example 3

Co-Localization of tRNA and the Factory-Forming NS2 Protein of the Ibaraki Virus Materials and Methods:

In addition to the materials and methods described above with respect to Example 1, the following materials and methods were used:

Virus—The Ibaraki Virus was isolated in September 1959, in Ibaraki, Japan. The virus was passaged for 21 times (8 passages in bovine embryo kidney cells, 3 passages in Bovine Kidney cells, and 8 passages in Hamster Lung cells).

Virus purification—IBAV-infected OK cells were collected 48 h post infection and pelleted at 4° C. The pellet was resuspended in 6 ml TNET Buffer (50 mM Tris-HCl pH 8.0, 0.2 M NaCl, 5 mM EDTA, 0.5% Triton X-100) and homogenized (10 strokes) using a Glass homogenizer (7 ml). The homogenate was layered onto a sucrose cushion comprised of 66% and 40% sucrose each prepared in 0.2M Tris. Samples were centrifuged in a Beckman Ultracentrifuge using a SW41 Rotor, at 23,000 rpm, 4° C. for 3 hours. Purified virus was extracted from the interface of the sucrose cushions and 10 mM Dithiothreitol (DTT) was added to prevent virus aggregation.

Virus infection—CHO cells seeded at $1 \times 10^5$ cells/well in 24 wells plate on coverslips, were infected with semi-purified Ibaraki virus (MOI=1) for 24 h, and transfected with labeled yeast tRNA. For protein synthesis assay, cells were seeded at $2 \times 10^5$ cells/well in 6 wells plate, infected the next day, and radio-labeled 30 h post infection.

Antibodies—Monoclonal mouse anti-NS2 antibodies were specially generated for the present study. Mice were immunized with the following peptide: n'-PEPKGYV- LEISEVGSYRIQDG-c' (corresponding to amino acids 51 to 71 of IBAV NS2, GeneScript Corporation (NJ, USA)).

FRET assay—Cells transfected with Rho110 (donor) and/or Cy3 (acceptor) bulk labeled yeast tRNA were fixed 7 h post transfection, mounted and imaged with a spinning disc confocal microscope. A raw FRET signal the recorded emission at 550-570 nm in response to illumination at 473 nm served as a basis for the calculated FRET (FRETc) signal [raw FRET signal after the elimination of background and of the non-specific contribution originating from the donor bleedthrough and the direct excitation of the acceptor under the FRET illumination conditions (calculated with the appropriate control samples)].

Figure 4A:
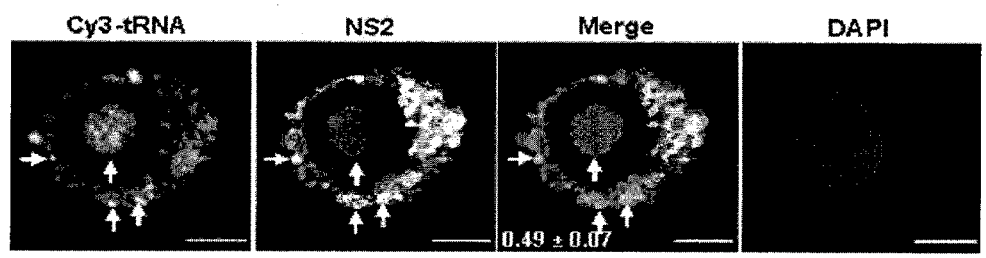
FIG. 4A depicts pictures of cells transfected with Cy3-labeled bulk tRNA following infection with Ibaraki virus.

Results:

A. CHO cells were infected with the Ibaraki virus (moi=1) and transfected at 30 h post infection with Cy3-labeled bulk yeast tRNA. At 6 h post transfection cells were fixed, immunostained with anti-NS2 and Alexa-488 goat-anti-mouse antibodies and imaged by confocal microscopy. The results, presented in FIG. 4A, shows tRNA signal (left hand panel), NS2 immunostain signal (second panel), merged image of the tRNA signal and the NS2 signal (third panel) and the DAPI signal (right hand panel). The results demonstrate that the labeled tRNA, showed a high and significant co-localization with NS2 (CCF of 0.49±0.07; CL=52±15%), both in the discrete cytoplasmic punctae as well as in the cell nucleus co localization of tRNA. Arrows point to typical co-localization occurrences in the imaged cell.

Figure 4B:
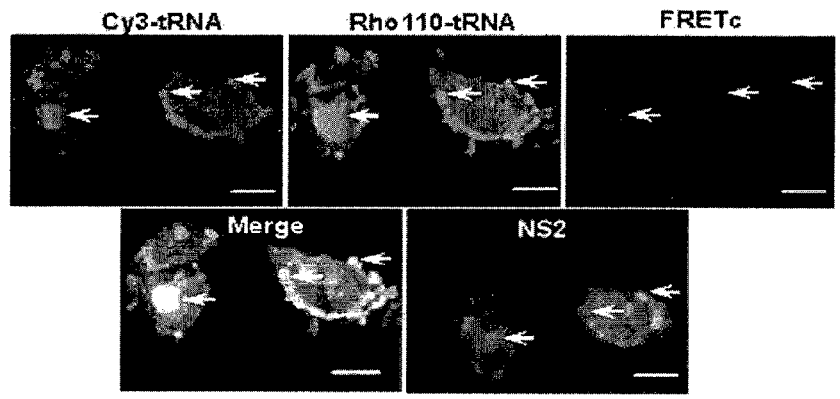
FIG. 4B depicts pictures of cells transfected with Cy3-tRNA and Rho110-tRNA following infection with Ibaraki virus.

B. CHO cells were infected with Ibaraki virus (MOI=1) and transfected at 30 h post infection with labeled tRNA (Rho110 and Cy3 labeled). At 6 h post transfection cells were fixed, immunostained with anti-NS2 and Alexa-647 goat-anti-mouse antibodies and imaged by confocal microscopy. FRET values were calculated as described in Materials and Methods. The results presented in FIG. 4B show that infected cells co-transfected with Rho-110-tRNA and Cy3-tRNA, and labeled for NS2, FRET signals can be observed in the proximity/overlap of viral factories, indicating the virally induced compartmentalization of active viral protein synthesis. Arrows point to typical triple co-localization occurrences in the imaged cell.

Figure 4C:
FIG. 4C depicts electron microscopy pictures of cells infected with Ibaraki virus: Left panel—entire cell (arrows indicate factories), center panel—a close-up of the viral factory with interspersed virions, right hand panel—accumulation of electron dense spots in the factory vicinity (ellipse points to typical accumulations).
Figure 4D:
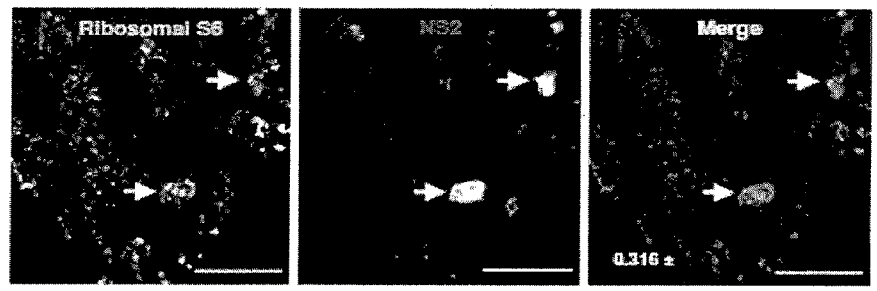
FIG. 4D depict electron microscopy pictures of cells infected with Ibaraki virus and stained with anti-NS2 and anti Ribosomal protein S6 antibodies (arrows point to typical instances of co-localization.

C. At 36 h post-infection, unique structures, interpreted as viral factories, consisting of an electron-dense matrix interspersed with icosahedral structured virions were present in different localizations in the cytosol of the cell (FIG. 4C, arrow). Typically, viral factories were surrounded with multiple layers of electron-dense spots, considerably smaller than the virions. To directly probe for the presence of ribosomes in the vicinities of factories, CHO cells, infected in identical conditions, were processed for immunofluorescence and concomitantly stained for NS2 and the ribosomal protein S6 (rpS6). A considerable amount of NS2 and rpS6 co-localized (70% and 28% of NS2 and rpS6, respectively, FIG. 4D) yielding a maximum cross-correlation coefficient (CCF) of 0.31, in accord with the FRET measurements and the EM analysis.

Example 4

Screening Stress-Causing Compounds

Screening for compounds with stress-causing activity or compounds alleviating cell stress: For the molecular entity assayed (the compound), a panel of primary cells or cell lines of interest (heart, muscle, kidney, liver, CNS, and the like) is prepared. The cells are transfected by the fluorescent labeled tRNA probes (essentially as described in Examples 1-3) and subjected to treatment by the compound being assayed. In some instances, the cells are triggered to exhibit cell stress prior to assaying the tested compound, in order to allow detection of reduced cell stress levels resulting from the treatment. Changes in stress response are then measured. Cells showing significant changes in stress indicate stress-related activity of the compound being assayed. For assaying a large panel of drug candidates (compounds) and/or a large number of cell types, the assay is performed in high-throughput systems using a cell-based assay reader such as the IN cell analyzer (GE healthcare), Celigo (Cyntellect Inc), Opera (Perkin-Elmer) and/or ImageXpress (Molecular Devices). Once a stress-causing activity is noted, the spectrum of stress responses across the cell lines may further be used for elucidating the mechanism underlying the stress effect caused by the tested compound.

What is claimed is:

1. A method for detection of anti-oxidant activity of a test compound, the method comprising:
   introducing a labeled tRNA into a cell;
   detecting the subcellular localization of the tRNA over a predetermined period of time, wherein the detection is based on the signal emitted from the labeled tRNA; and
   detecting a change in the subcellular localization of the labeled tRNA in the cell after exposure of the cell to the test compound, wherein the change is indicative of anti-oxidant induced stress in the cell.

2. The method of claim 1, wherein the subcellular localization comprises nuclear localization, cytoplasmic localization, or both.

3. The method of claim 2, wherein decreased subcellular nuclear localization of the labeled tRNA and/or increased subcellular cytoplasmic localization of the labeled tRNA is indicative of increased anti-oxidant activity of the test compound.

4. The method of claim 1, wherein the test compound is selected from a drug, a substance, a chemical moiety, a peptide, or any combination thereof.

5. The method of claim 1, wherein the labeled tRNA comprises fluorescently labeled tRNA.

6. The method of claim 5, wherein the fluorescently labeled tRNA comprises Cy3-tRNA, Rho-110-tRNA, Cy5-tRNA, alexa-based fluorophores, small organic fluorophores, or any combination thereof.

7. The method of claim 1, wherein detecting comprises imaging method, biochemical method, or both.

8. The method of claim 1, wherein the cell is selected from a primary cell, tissue culture cell, mammalian cell, yeast cell, avian cell, a plant cell or another eukaryotic cell type.

9. The method of claim 1, wherein the method further comprises detecting a marker of a subcellular compartment, said marker comprises: a dye, an antibody, an antigen, a protein, an organelle, or any combination thereof.

10. The method of claim 1, wherein the method is qualitative, quantitative, or both.

11. The method of claim 1, wherein the method is performed in real time or performed using time lapse localization on a series of fixated cells.

12. The method of claim 1, wherein the change in the subcellular localization of the labeled tRNA is a temporal change, a spatial change, or both.

13. The method of claim 1, wherein the tRNA is selected from the group consisting of mammalian tRNA, yeast tRNA, bacterial tRNA, avian tRNA, plant tRNA and derivatives and combinations thereof.

14. A system for the detection of anti-oxidant activity of a test compound, the system comprising:

a living cell having a labeled tRNA introduced thereto;

a detection device adapted to detect the subcellular localization of the tRNA over a predetermined period of time, wherein the detection is based on a signal emitted from the labeled tRNA, said device is further configured to detect a change in the subcellular localization of the labeled tRNA in the cell after exposure of the cell to the test compound, wherein the change is indicative of antioxidant stress to the cell; and an enclosed chamber adapted to provide the cell with controlled growing conditions.

15. The system of claim 14, wherein the subcellular localization comprises nuclear localization, cytoplasmic localization, or both.

16. The system of claim 15, wherein increased subcellular nuclear localization of the labeled tRNA or decreased subcellular cytoplasmic localization is indicative of increased antioxidant activity of the test compound.

17. The system of claim 14, wherein the labeled tRNA comprises fluorescently labeled tRNA, the fluorescently labeled tRNA comprises Cy3-tRNA, Rho-110-tRNA, Cy5-tRNA, small organic fluorophore-tRNA, or any combination thereof.

18. The system of claim 14, wherein the detection device comprises an imaging device, selected from a camera, a confocal microscope, a fluorescence microscope, or any combination thereof.

19. The system of claim 14, wherein said detection device further adapted to detect a marker of a subcellular compartment.

20. The system of claim 14, wherein said controlled growing conditions comprises: pH, temperature, humidity, $CO_2$ levels, oxygen saturation, medium type, illumination, ventilation, or any combination thereof.

* * * * *